(12) United States Patent
Kasai et al.

(10) Patent No.: US 11,305,422 B2
(45) Date of Patent: Apr. 19, 2022

(54) CONTROL APPARATUS AND CONTROL METHOD

(71) Applicant: SONY CORPORATION, Tokyo (JP)

(72) Inventors: Takara Kasai, Kanagawa (JP); Daisuke Nagao, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 333 days.

(21) Appl. No.: 16/086,952

(22) PCT Filed: Feb. 2, 2017

(86) PCT No.: PCT/JP2017/003691
§ 371 (c)(1),
(2) Date: Sep. 20, 2018

(87) PCT Pub. No.: WO2017/169082
PCT Pub. Date: Oct. 5, 2017

(65) Prior Publication Data
US 2019/0091861 A1   Mar. 28, 2019

(30) Foreign Application Priority Data
Mar. 29, 2016   (JP) .............................. JP2016-065153

(51) Int. Cl.
*B25J 9/16*   (2006.01)
*G05B 13/04*   (2006.01)
(Continued)

(52) U.S. Cl.
CPC ............. *B25J 9/1633* (2013.01); *A61B 34/30* (2016.02); *B25J 13/085* (2013.01); *B25J 13/088* (2013.01);
(Continued)

(58) Field of Classification Search
CPC ...... B25J 9/1633; B25J 13/085; B25J 13/088; B25J 19/06; G05B 13/048;
(Continued)

(56) References Cited

U.S. PATENT DOCUMENTS 8,090,475 B2 *   1/2012   Blanc ..................... B25J 9/1674
                                              700/261
8,649,904 B2 *   2/2014   Sasai ..................... B25J 9/1674
                                              700/254
(Continued)

FOREIGN PATENT DOCUMENTS

CN      106063090 A        10/2016
DE    102013203426 A1      10/2013
(Continued)

OTHER PUBLICATIONS

Featherstone, Roy. Rigid Body Dynamics Algorithms. 1st ed. 2008. New York, NY: Springer US, 2008. Web. (Year: 2008).*
(Continued)

*Primary Examiner* — Yoshihisa Ishizuka
*Assistant Examiner* — Carter W Ferrell
(74) *Attorney, Agent, or Firm* — Chip Law Group

(57) ABSTRACT

To accurately predict a sensor value even in the case where external force is received. A control apparatus according to the present disclosure includes a prediction section that, in an actuator including a torque sensor that detects torque generated at a driving shaft, and an encoder that detects a rotational angle of the driving shaft, predicts a detection value of the encoder on a basis of a detection value of the torque sensor, or predict the detection value of the torque sensor on a basis of the detection value of the encoder, and a trouble determination section that compares a prediction value predicted by the prediction section with an actually measured value of the torque sensor or the encoder to
(Continued)

perform trouble determination on the torque sensor or the encoder.

13 Claims, 14 Drawing Sheets

(51) Int. Cl.
| | |
|---|---|
| A61B 34/30 | (2016.01) |
| H02P 6/34 | (2016.01) |
| H02P 29/024 | (2016.01) |
| B25J 19/06 | (2006.01) |
| B25J 13/08 | (2006.01) |
| H02P 23/12 | (2006.01) |
| G01R 1/00 | (2006.01) |
| G05B 19/4155 | (2006.01) |
| A61B 90/30 | (2016.01) |
| A61B 90/00 | (2016.01) |

(52) U.S. Cl.
CPC .............. *B25J 19/06* (2013.01); *G01R 1/00* (2013.01); *G05B 13/048* (2013.01); *G05B 19/4155* (2013.01); *H02P 6/34* (2016.02); *H02P 23/12* (2013.01); *H02P 29/0241* (2016.02); *A61B 2090/066* (2016.02); *A61B 2090/309* (2016.02); *A61B 2090/371* (2016.02); *G05B 2219/39188* (2013.01); *G05B 2219/40148* (2013.01); *G05B 2219/50391* (2013.01)

(58) Field of Classification Search
CPC ...... G05B 19/4155; G05B 2219/50391; G05B 2219/40148; G05B 2219/39188; A61B 34/30; A61B 2090/066; A61B 2090/067; A61B 2090/309; A61B 2090/371; H02P 29/0241; H02P 23/12; H02P 6/34; G01R 1/00

See application file for complete search history.

(56) References Cited

U.S. PATENT DOCUMENTS

| | | | | |
|---|---|---|---|---|
| 9,205,560 | B1* | 12/2015 | Edsinger | ............. G05B 19/4062 |
| 2013/0038342 | A1* | 2/2013 | Nozaki | ............... H02P 29/0241 |
| | | | | 324/750.3 |
| 2013/0073085 | A1* | 3/2013 | Oaki | ...................... B25J 9/1633 |
| | | | | 700/258 |
| 2013/0270053 | A1 | 10/2013 | Orita | |
| 2015/0057799 | A1* | 2/2015 | Ueberle | ................. B25J 9/1674 |
| | | | | 700/253 |
| 2015/0250547 | A1* | 9/2015 | Fukushima | ............ B25J 9/1697 |
| | | | | 606/130 |
| 2015/0256113 | A1* | 9/2015 | Takase | .................... H02P 27/04 |
| | | | | 318/400.02 |
| 2016/0365771 | A1 | 12/2016 | Kokubo et al. | |
| 2017/0066131 | A1* | 3/2017 | Kamikawa | ............. B25J 9/1697 |

FOREIGN PATENT DOCUMENTS

| | | | |
|---|---|---|---|
| EP | 3109980 A1 | | 12/2016 |
| JP | 06289938 A | * | 10/1994 |
| JP | 2006-116635 A | | 5/2006 |
| JP | 2007-301691 A | | 11/2007 |
| JP | 2007301691 A | * | 11/2007 |
| JP | 2013-220496 A | | 10/2013 |
| WO | 2015/133291 A1 | | 9/2015 |
| WO | 2015/137040 A1 | | 9/2015 |

OTHER PUBLICATIONS

International Search Report and Written Opinion of PCT Application No. PCT/JP2017/003691, dated Apr. 18, 2017, 09 pages of ISRWO.

* cited by examiner

CONTROL APPARATUS AND CONTROL METHOD

CROSS REFERENCE TO RELATED APPLICATIONS

This application is a U.S. National Phase of International Patent Application No. PCT/JP2017/003691 filed on Feb. 2, 2017, which claims priority benefit of Japanese Patent Application No. JP 2016-065153 filed in the Japan Patent Office on Mar. 29, 2016. Each of the above-referenced applications is hereby incorporated herein by reference in its entirety.

TECHNICAL FIELD

The present disclosure relates a control apparatus and a control method.

BACKGROUND ART

Conventionally, for example, Patent Literature 1 below has described technology that relates to a control apparatus for a robot, and is supposed to use a dynamic simulation to predict the operations of all joints.

CITATION LIST

Patent Literature

Patent Literature 1: JP 2006-116635A

DISCLOSURE OF INVENTION

Technical Problem

However, the technology described in Patent Literature above has a problem that it is impossible to predict a sensor value indicating the operation of a joint in the case where there is an interaction with the external world such as the case where external force is received.

It is then desired to accurately predict a sensor value even in the case where external force is received.

Solution to Problem

According to the present disclosure, there is provided a control apparatus including: a prediction section configured to, in an actuator including a torque sensor that detects torque generated at a driving shaft, and an encoder that detects a rotational angle of the driving shaft, predict a detection value of the encoder on a basis of a detection value of the torque sensor, or predict the detection value of the torque sensor on a basis of the detection value of the encoder; and a trouble determination section configured to compare a prediction value predicted by the prediction section with an actually measured value of the torque sensor or the encoder to perform trouble determination on the torque sensor or the encoder.

The prediction section may use torque and external force generated by the actuator at the driving shaft to predict the detection value of the encoder or the detection value of the torque sensor on a basis of an equation of motion that defines a relationship between the torque generated at the driving shaft, angular velocity of the actuator, and angular acceleration of the actuator.

In addition, the trouble determination section may perform the trouble determination in a case where a difference between a value predicted by the prediction section and an actually measured value of the torque sensor or the encoder is greater than or equal to a predetermined threshold.

In addition, according to the present disclosure, there is provided a control method including: predicting, in an actuator including a torque sensor that detects torque generated at a driving shaft, and an encoder that detects a rotational angle of the driving shaft, a detection value of the encoder on a basis of a detection value of the torque sensor, or predicting the detection value of the torque sensor on a basis of the detection value of the encoder; and comparing the predicted value with an actually measured value of the torque sensor or the encoder to perform trouble determination on the torque sensor or the encoder.

Advantageous Effects of Invention

According to the present disclosure as described above, it is possible to accurately predict a sensor value even in the case where external force is received.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
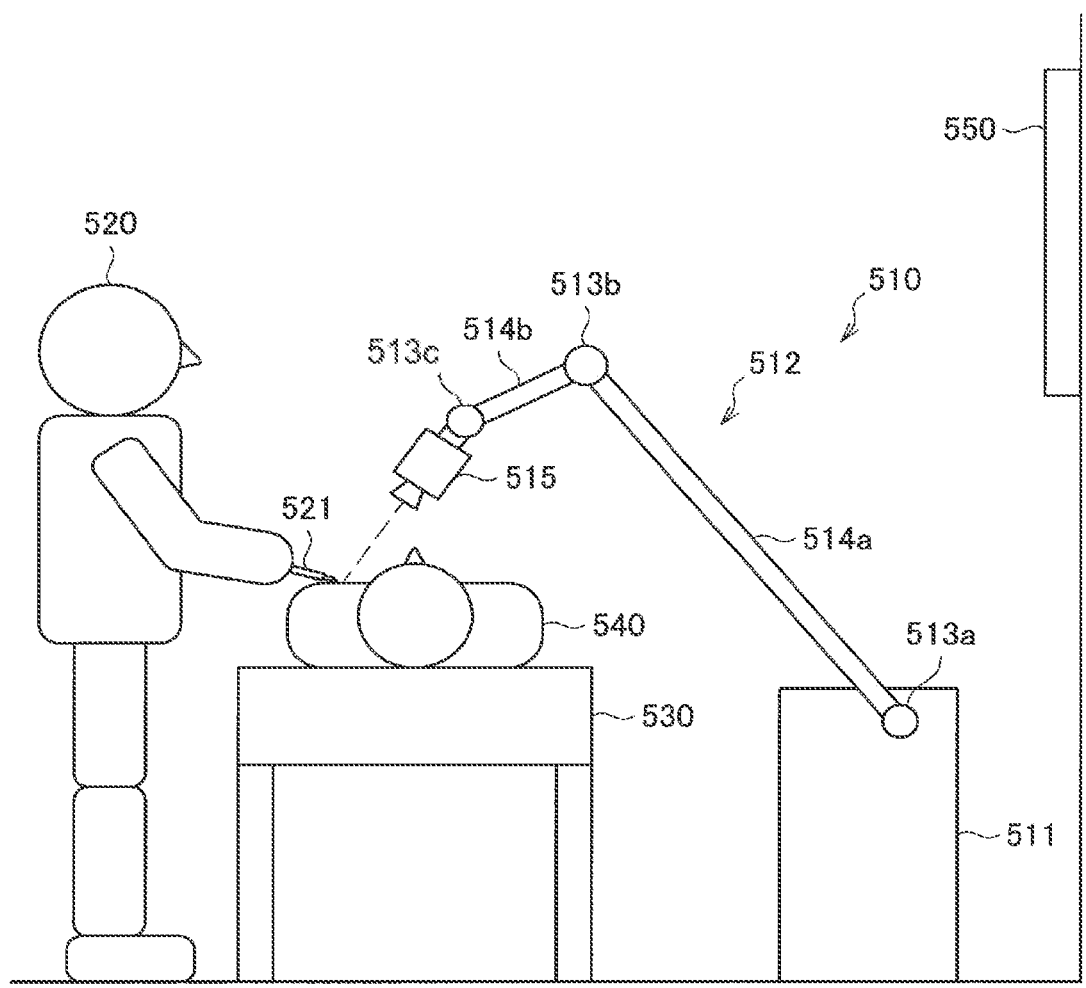
FIG. 1 is an explanatory diagram for describing an application example of using a supporting arm apparatus according to an embodiment of the present disclosure for a medical purpose.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will proceed in the following order.
1. Review of medical supporting arm apparatus
2. Embodiment of present disclosure
2-1. External appearance of supporting arm apparatus
2-2. Generalized inverse dynamics
2-2-1. Virtual force calculating process
2-2-1. Actual force calculating process
2-3. Ideal joint control
2-4. Configuration of supporting arm control system
2-5. Regarding sensor value estimation and trouble determination
3. Application example
4. Feature of trouble determination according to present embodiment
5. Hardware configuration
6. Conclusion

1. Review of Medical Supporting Arm Apparatus

First, the background in which the inventors have developed the present disclosure will be described in order to further clarify the present disclosure.

An application example of using a supporting arm apparatus according to an embodiment of the present disclosure for a medical purpose will be described with reference to FIG. 1. FIG. 1 is an explanatory diagram for describing an application example of using a supporting arm apparatus according to an embodiment of the present disclosure for a medical purpose.

FIG. 1 schematically illustrates an exemplary medical procedure using the supporting arm apparatus according to the present embodiment. Specifically, FIG. 1 illustrates an example in which a doctor serving as a practitioner (user) 520 performs surgery on a medical procedure target (patient) 540 on a medical procedure table 530, for example, using surgical instruments 521 such as a scalpel, tweezers, and forceps. Note that, in the following description, the medical procedure refers to a general concept including various kinds of medical treatments that the doctor serving as the user 520 performs on the patient of the medical procedure target 540 such as surgery or an examination. Further, the example of FIG. 1 illustrates surgery as an example of the medical procedure, but the medical procedure using a supporting arm apparatus 510 is not limited to surgery and may be various kinds of other medical procedures such as an examination using an endoscope.

The supporting arm apparatus 510 according to the present embodiment is installed at the side of the medical procedure table 530. The supporting arm apparatus 510 includes a base section 511 serving as a base and an arm section 512 extending from the base section 511. The arm section 512 includes a plurality of joint sections 513a, 513b, 513c, a plurality of links 514a and 514b coupled by the joint sections 513a and 513b, and an imaging unit 515 installed at the front edge of the arm section 512. In the example illustrated in FIG. 1, for the sake of simplification, the arm section 512 includes the 3 joint sections 513a to 513c and the 2 links 514a and 514b, but practically, for example, the number and the shape of the joint sections 513a to 513c and the links 514a and 514b and a direction of the driving shaft of the joint sections 513a to 513c may be appropriately set to express a desired degree of freedom in view of a degree of freedom of the position and posture of the arm section 512 and the imaging unit 515.

The joint sections 513a to 513c have a function of coupling the links 514a and 514b to be rotatable, and as the joint sections 513a to 513c are rotationally driven, driving of the arm section 512 is controlled. Here, in the following description, the position of each component of the supporting arm apparatus 510 is the position (coordinates) in a space specified for driving control, and the posture of each component is a direction (angle) to an arbitrary axis in a space specified for driving control. Further, in the following description, driving (or driving control) of the arm section 512 refers to changing (controlling a change of) the position and posture of each component of the arm section 512 by performing driving (or driving control) of the joint sections 513a to 513c and driving (or driving control) of the joint sections 513a to 513c.

Various kinds of medical apparatuses are connected to the front edge of the arm section 512 as the front edge unit. In the example illustrated in FIG. 1, the imaging unit 515 is installed at the front edge of the arm section 512 as an exemplary front edge unit. The imaging unit 515 is a unit that acquires an image (a photographed image) of a photographing target and is, for example, a camera capable of capturing a moving image or a still image. As illustrated in FIG. 1, the posture or the position of the arm section 512 and the imaging unit 515 is controlled by the supporting arm apparatus 510 such that the imaging unit 515 installed at the front edge of the arm section 512 photographs a state of a medical procedure part of the medical procedure target 540. Note that the front edge unit installed at the front edge of the arm section 512 is not limited to the imaging unit 515 and may be various kinds of medical apparatuses. For example, the medical apparatus includes various kinds of units used when the medical procedure is performed such as an endoscope, a microscope, a unit having an imaging function such as the imaging unit 515, various kinds of medical procedure instruments, and an examination apparatus. As described above, the supporting arm apparatus 510 according to the present embodiment is a medical supporting arm apparatus equipped with a medical apparatus. Further, a stereo camera having two imaging units (camera units) may be installed at the front edge of the arm section 512, and may perform photography so that an imaging target is displayed as a three dimensional (3D) image. Note that the supporting arm apparatus 510 provided with camera units such as the imaging unit 515 for imaging a surgical site and the stereo camera as front edge units will also be referred to as video microscope (VM) supporting arm apparatus.

Further, a display apparatus 550 such as a monitor or a display is installed at a position facing the user 520. The captured image of the medical procedure part captured by the imaging unit 515 is displayed on a display screen of the display apparatus 550. The user 520 performs various kinds of treatments while viewing the captured image of the medical procedure part displayed on the display screen of the display apparatus 550.

As described above, in the present embodiment, in the medical field, a technique of performing surgery while photographing the medical procedure part through the supporting arm apparatus 510 is proposed. Here, in various kinds of medical procedures including surgery, it is necessary to reduce fatigue or a burden on the user 520 and the patient 540 by performing the medical procedure efficiently. In order to satisfy such a demand, in the supporting arm apparatus 510, for example, the following capabilities are considered desirable.

First, as a first point, the supporting arm apparatus 510 should secure a task space for surgery. If the arm section 512 or the imaging unit 515 hinders a field of vision of the practitioner or impedes motion of a hand performing a treatment while the user 520 is performing various kinds of treatments on the medical procedure target 540, the efficiency of surgery is lowered. Further, in FIG. 1, although not illustrated, in an actual surgical scene, for example, a plurality of other doctors and/or nurses performing various support tasks of handing an instrument to the user 520 or checking various kinds of vital signs of the patient 540 are commonly around the user 520 and the patient 540, and there are other apparatuses for performing the support tasks, and thus a surgical environment is complicated. Thus, a small size is desirable in the supporting arm apparatus 510.

Next, as a second point, the supporting arm apparatus 510 should have high operability for moving the imaging unit 515. For example, the user 520 may desire to observe the same medical procedure part at various positions and angles while performing a treatment on the medical procedure part according to a surgical part or surgical content. In order to change an angle at which the medical procedure part is observed, it is necessary to change an angle of the imaging unit 515 with respect to the medical procedure part, but at this time, it is more desirable that only a photographing angle be changed in a state in which the photographing direction of the imaging unit 515 is fixed to the medical procedure part (that is, while photographing the same part). Thus, for example, the supporting arm apparatus 510 should have operability of a high degree of freedom such as a turning movement (a pivot movement) in which the imaging unit 515 moves within a surface of a cone having the medical procedure part as an apex, and an axis of the cone is used as a pivot axis in the state in which the photographing direction of the imaging unit 515 is fixed to the medical procedure part. Since the photographing direction of the imaging unit 515 is fixed to a certain medical procedure part, the pivot movement is also called point lock movement.

Further, in order to change the position and the angle of the imaging unit 515, for example, a method in which the user 520 manually moves the arm section 512 to move the imaging unit 515 to a desired position and at a desired angle is considered. Thus, it is desirable that there be operability enabling movement of the imaging unit 515, the pivot movement, or the like to be easily performed even with one hand.

Further, there may be a demand from the user 520 to move a photographing center of a captured image captured by the imaging unit 515 from a part on which a treatment is being performed to another part (for example, a part on which a next treatment will be performed) while performing a treatment with both hands during surgery. Thus, various driving methods of the arm section 512 are necessary such as a method of controlling driving of the arm section 512 by an operation input from an input section such as a pedal as well as a method of controlling driving of the arm section 512 by a manual motion when it is desired to change the position and posture of the imaging unit 515.

As described above as the capability of the second point, the supporting arm apparatus 510 should have high operability enabling easy movement, for example, by the pivot movement or the manual motion and satisfying intuition or a desire of the user 520.

Lastly, as a third point, the supporting arm apparatus 510 should have stability in the driving control of the arm section 512. The stability in the driving control of the arm section 512 may be stability in the position and posture of the front edge unit when the arm section 512 is driven. Further, the stability in the driving control of the arm section 512 also includes smooth movement and suppression of vibration (vibration suppression) of the front edge unit when the arm section 512 is driven. For example, when the front edge unit is the imaging unit 515 as in the example illustrated in FIG. 1, if the position or the posture of the imaging unit 515 is unstable, the captured image displayed on the display screen of the display apparatus 550 is unstable, and the user may have a feeling of discomfort. Particularly, when the supporting arm apparatus 510 is used for surgery, a use method in which a stereo camera including two imaging units (camera units) is installed as the front edge unit, and a 3D image generated on the basis of photographed images obtained by the stereo camera is displayed can be assumed. As described above, when the 3D image is displayed, if the position or the posture of the stereo camera is unstable, the user is likely to experience 3D sickness. Further, an observation range photographed by the imaging unit 515 may be enlarged up to about φ15 mm depending on a surgical part or surgical content. When the imaging unit 515 enlarges and photographs a narrow range as described above, slight vibration of the imaging unit 515 is shown as a large shake or deviation of an imaged image. Thus, high positioning accuracy with a permissible range of about 1 mm is necessary for driving control of the arm section 512 and the imaging unit 515. As described above, high-accuracy responsiveness and high positioning accuracy are necessary in driving control of the arm section 512.

The inventors have reviewed existing general balance arms and supporting arm apparatuses based on position control in terms of the above-mentioned 3 capabilities.

First, with regard to securing the task space for the surgery of the first point, in the general balance arm, a counter balance weight (also called a counter weight or a balancer) for maintaining balance of force when the arm section is moved is installed inside the base section or the like, and thus it is difficult to reduce the size of the balance arm apparatus, and it is difficult to say that the corresponding capability is fulfilled.

Further, with regard to the high operability of the second point, in the general balance arm, only some driving of the arm section, for example, only biaxial driving for moving the imaging unit on a (two-dimensional) plane is electric driving, and manual positioning is necessary for movement of the arm section and the imaging unit, and thus it is difficult to say that high operability can be implemented. Further, in the general supporting arm apparatus based on the position control, since it is difficult to flexibly deal with external force by the position control used for driving control of the arm section, that is, control of the position and posture of the imaging unit, the position control is commonly called "hard control" and is not suitable of implementing desired operability satisfying the user's intuition.

Further, with regard to stability in driving control of the arm section of the third point, the joint section of the arm section generally has factors that are not easily modelized such as friction, inertia, and the like. In the general balance arm or the supporting arm apparatus based on the position control, the factors serve as a disturbance in the driving control of the joint section, and even when a theoretically appropriate control value (for example, a current value applied to a motor of the joint section) is given, there are cases in which desired driving (for example, rotation at a desired angle in the motor of the joint section) is not implemented, and it is difficult to implement high stability necessary for driving control of the arm section.

As described above, the inventors have reviewed supporting arm apparatuses being used for medical purposes and learned that there is a demand for the capabilities of the above-mentioned three points with regard to the supporting arm apparatus. However, it is difficult for the general balance arm or the supporting arm apparatus based on the position control to easily fulfill such capabilities. The inventors have developed a supporting arm apparatus, a supporting arm control system, a supporting arm control method, and a program according to the present disclosure as a result of reviewing configurations satisfying the capabilities of the three points. Hereinafter, preferred embodiments of the configuration developed by the inventors will be described in detail.

2. Embodiment of Present Disclosure

A supporting arm control system according to an embodiment of the present disclosure will be described below. In the supporting arm control system according to the present embodiment, driving of a plurality of joint sections installed in the supporting arm apparatus is controlled by whole body cooperative control using generalized inverse dynamics. Further, ideal joint control of implementing an ideal response to a command value by correcting influence of a disturbance is applied to driving control of the joint section.

In the following description of the present embodiment, an external appearance of the supporting arm apparatus according to the present embodiment and a schematic configuration of the supporting arm apparatus will be first described in [2-1. External appearance of supporting arm apparatus]. Then, an overview of the generalized inverse dynamics and the ideal joint control used for control of the supporting arm apparatus according to the present embodiment will be described in [2-2. Generalized inverse dynamics] and [2-3. Ideal joint control]. Then, a configuration of a system for controlling the supporting arm apparatus according to the present embodiment will be described with reference to a functional block diagram in [2-4. Configuration of supporting arm control system]. Lastly, a specific example of the whole body cooperative control using the generalized inverse dynamics in the supporting arm apparatus according to the present embodiment will be described in [2-5. Specific example of purpose of motion].

Note that the following description will proceed with an example in which a front edge unit of an arm section of a supporting arm apparatus according to an embodiment of the present disclosure is an imaging unit, and a medical procedure part is photographed by the imaging unit during surgery as illustrated in FIG. 1 as an embodiment of the present disclosure, but the present embodiment is not limited to this example. The supporting arm control system according to the present embodiment can be applied even when a supporting arm apparatus including a different front edge unit is used for another purpose.

2-1. External Appearance of Supporting Arm Apparatus

Figure 2:
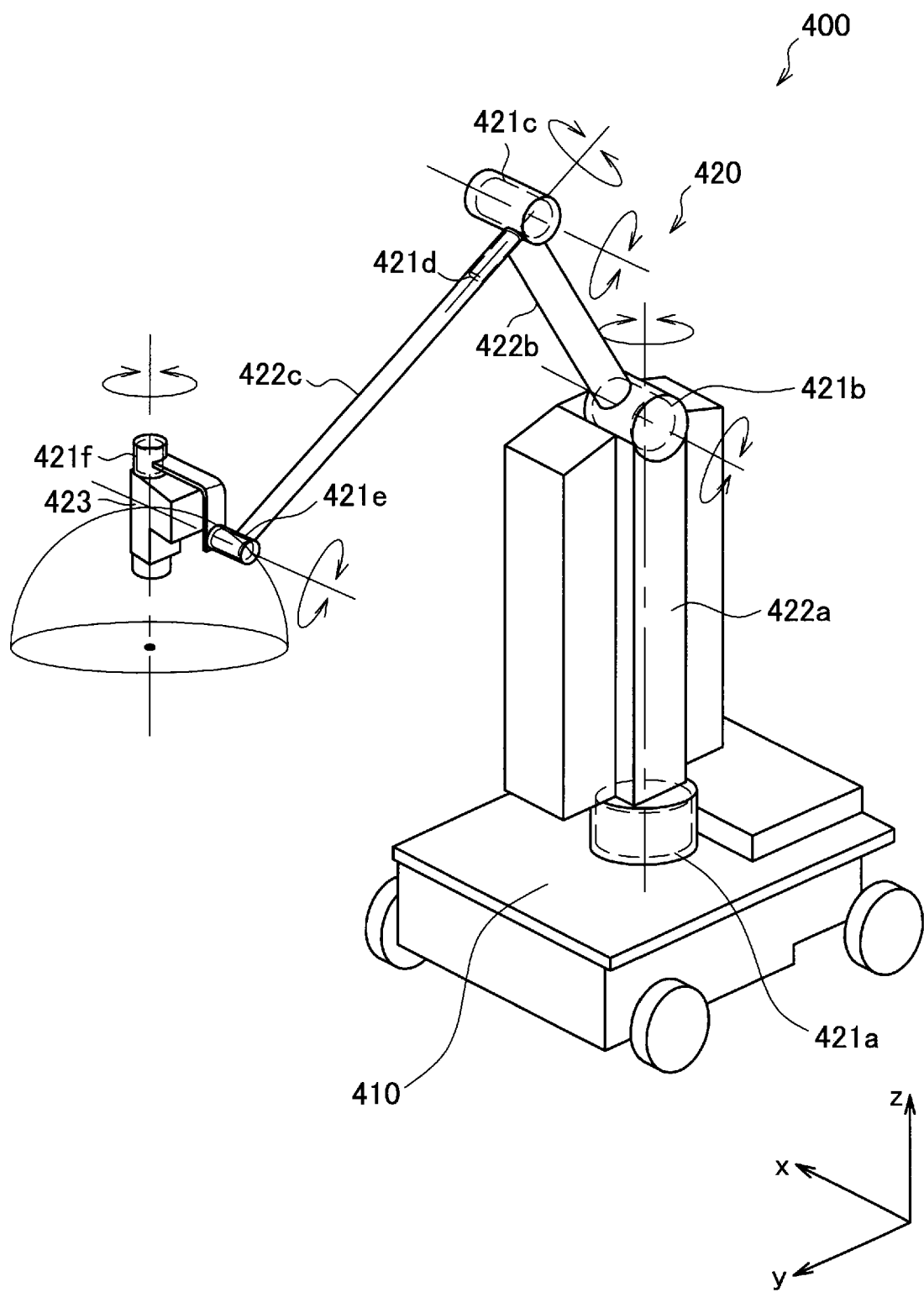
FIG. 2 is a schematic diagram illustrating an external appearance of a supporting arm apparatus according to an embodiment of the present disclosure.

First, a schematic configuration of a supporting arm apparatus according to an embodiment of the present disclosure will be described with reference to FIG. 2. FIG. 2 is a schematic diagram illustrating an external appearance of a supporting arm apparatus according to an embodiment of the present disclosure.

Referring to FIG. 2, a supporting arm apparatus 400 according to the present embodiment includes a base section 410 and an arm section 420. The base section 410 serves as the base of the supporting arm apparatus 400, and the arm section 420 extends from the base section 410. Further, although not illustrated in FIG. 2, a control section that controls the supporting arm apparatus 400 in an integrated manner may be installed in the base section 410, and driving of the arm section 420 may be controlled by the control section. For example, the control section includes various kinds of signal processing circuits such as a central processing unit (CPU) or a digital signal processor (DSP).

The arm section 420 includes a plurality of joint sections 421$a$ to 421$f$, a plurality of links 422$a$ to 422$c$ that are coupled with one another by the joint sections 421$a$ to 421$f$, and an imaging unit 423 installed at the front edge of the arm section 420.

The links 422$a$ to 422$c$ are rod-like members, one end of the link 422$a$ is coupled with the base section 410 through the joint section 421$a$, the other end of the link 422$a$ is coupled with one end of the link 422$b$ through the joint section 421$b$, and the other end of the link 422$b$ is coupled with one end of the link 422$c$ through the joint sections 421$c$ and 421$d$. Further, the imaging unit 423 is coupled to the front edge of the arm section 420, that is, the other end of the link 422$c$ through the joint sections 421$e$ and 421$f$. As described above, the arm shape extending from the base section 410 is configured such that the base section 410 serves as a support point, and the ends of the plurality of links 422$a$ to 422$c$ are coupled with one another through the joint sections 421$a$ to 421$f$.

The imaging unit 423 is a unit that acquires an image of a photographing target, and is, for example, a camera that captures a moving image, a still image. The driving of the arm section 420 is controlled such that the position and posture of the imaging unit 423 are controlled. In the present embodiment, for example, the imaging unit 423 photographs some regions of the body of the patient serving as the medical procedure part. Here, the front edge unit installed at the front edge of the arm section 420 is not limited to the imaging unit 423, and various kinds of medical apparatuses may be connected to the front edge of the arm section 420 as the front edge unit. As described above, the supporting arm apparatus 400 according to the present embodiment is a medical supporting arm apparatus equipped with a medical apparatus.

Here, the description of the supporting arm apparatus 400 will proceed with coordinate axes defined as illustrated in FIG. 2. Further, a vertical direction, a longitudinal direction, and a horizontal direction are defined according to the coordinate axes. In other words, a vertical direction with respect to the base section 410 installed on the floor is defined as a z axis direction and a vertical direction. Further, a direction along which the arm section 420 extends from the base section 410 as a direction orthogonal to the z axis (that is, a direction in which the imaging unit 423 is positioned with respect to the base section 410) is defined as a y axis direction and a longitudinal direction. Furthermore, a direction that is orthogonal to the y axis and the z axis is an x axis direction and a horizontal direction.

The joint sections 421a to 421f couple the links 422a to 422c to be rotatable. Each of the joint sections 421a to 421f includes a rotation mechanism that includes an actuator and is rotationally driven on a certain rotary axis according to driving of the actuator. By controlling rotary driving in each of the joint sections 421a to 421f, for example, it is possible to control driving of the arm section 420 to extend or shorten (fold) the arm section 420. Here, driving of the joint sections 421a to 421f is controlled by the whole body cooperative control which will be described in [2-2. Generalized inverse dynamics] and the ideal joint control which will be described in [2-3. Ideal joint control]. Further, as described above, since the joint sections 421a to 421f according to the present embodiment include the rotation mechanism, in the following description, driving control of the joint sections 421a to 421f specifically means controlling a rotational angle and/or generated torque (torque generated by the joint sections 421a to 4210 of the joint sections 421a to 421f.

The supporting arm apparatus 400 according to the present embodiment includes the 6 joint sections 421a to 421f, and implements 6 degrees of freedom with regard to driving of the arm section 420. Specifically, as illustrated in FIG. 2, the joint sections 421a, 421d, and 421f are installed such that the long axis directions of the links 422a to 422c connected thereto and the photographing direction of the imaging unit 473 connected thereto are set as the rotary axis direction, and the joint sections 421b, 421c, and 421e are installed such that an x axis direction serving as a direction in which connection angles of the links 422a to 422c and the imaging unit 473 coupled thereto are changed within a y-z plane (a plane specified by the y axis and the z axis) is set as the rotary axis direction. As described above, in the present embodiment, the joint sections 421a, 421d, and 421f have a function of performing yawing, and the joint sections 421b, 421c, and 421e have a function of performing pitching.

As the above-described configuration of the arm section 420 is provided, the supporting arm apparatus 400 according to the present embodiment can implement the 6 degrees of freedom on driving of the arm section 420, and thus can freely move the imaging unit 423 within a movable region of the arm section 420. FIG. 2 illustrates a hemisphere as an exemplary movable region of the imaging unit 423. When the central point of the hemisphere is the photographing center of the medical procedure part photographed by the imaging unit 423, the medical procedure part can be photographed at various angles by moving the imaging unit 423 on the spherical surface of the hemisphere in a state in which the photographing center of the imaging unit 423 is fixed to the central point of the hemisphere.

A configuration of the joint sections 421a to 421f illustrated in FIG. 2 will be described herein in further detail with reference to FIG. 3. Further, a configuration of an actuator serving as a component mainly related to the rotary driving of the joint sections 421a to 421f among the components of the joint sections 421a to 421f will be described herein with reference to FIG. 3.

Figure 3:
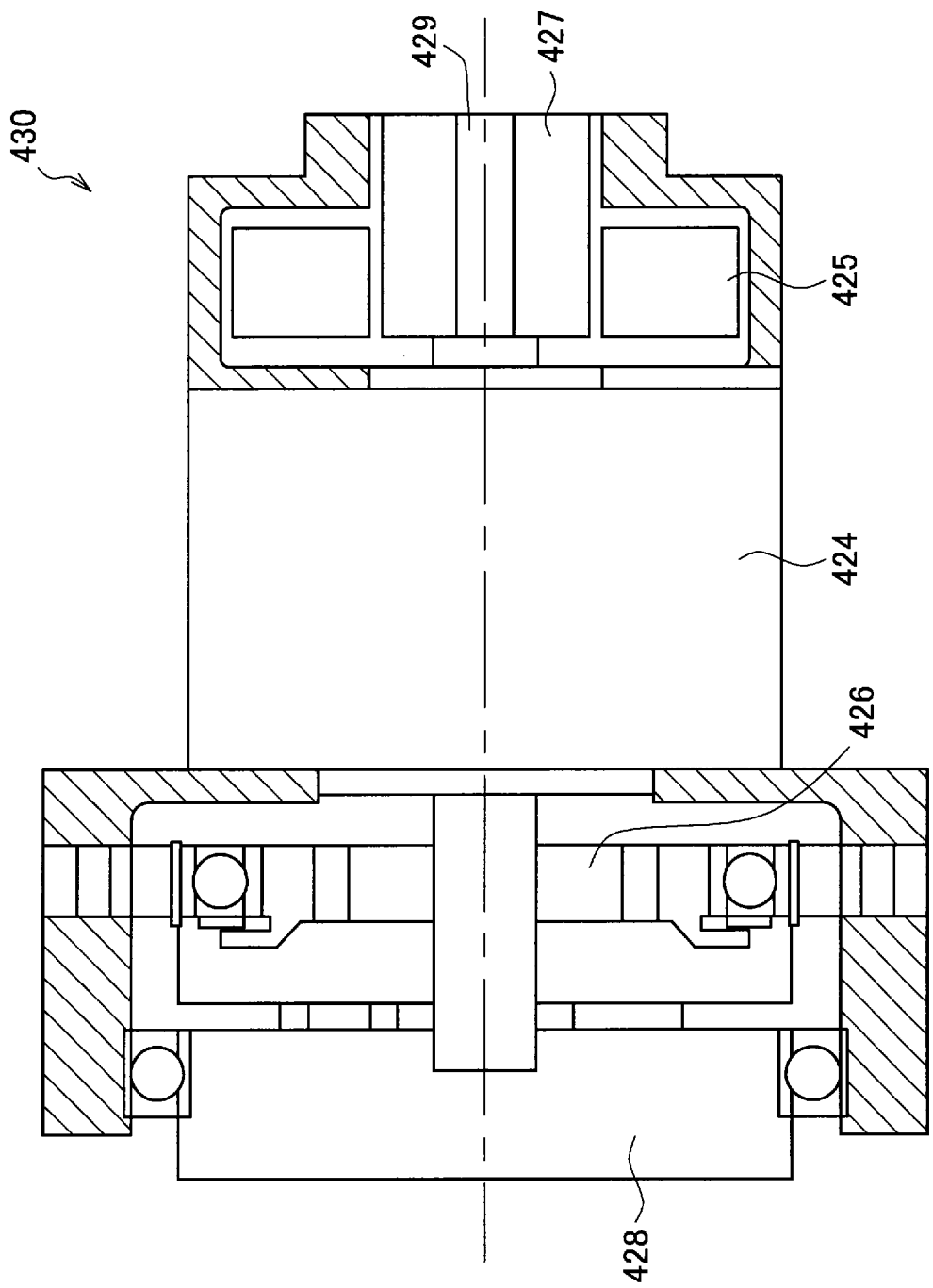
FIG. 3 is a cross-sectional diagram schematically illustrating a state in which an actuator of a joint section according to an embodiment of the present disclosure is cut along a cross section passing through a rotary axis.

FIG. 3 is a cross-sectional diagram schematically illustrating a state in which an actuator of each of the joint sections 421a to 421f according to an embodiment of the present disclosure is cut along a cross section passing through the rotary axis. Note that FIG. 3 illustrates an actuator among the components of the joint sections 421a to 421f, but the joint sections 421a to 421f may have any other component. For example, the joint sections 421a to 421f have various kinds of components necessary for driving of the arm section 420 such as a control section for controlling driving of the actuator and a support member for connecting and supporting the links 422a to 422c and the imaging unit 423 in addition to the components illustrated in FIG. 3. Further, in the above description and the following description, driving of the joint section of the arm section may mean driving of the actuator in the joint section.

Note that, as described above, in the present embodiment, driving of the joint sections 421a to 421f is controlled by the ideal joint control which will be described later in [2-3. Ideal joint control]. Thus, the actuator of the joint sections 421a to 421f illustrated in FIG. 3 is configured to perform driving corresponding to the ideal joint control. Specifically, the actuator of the joint sections 421a to 421f is configured to be able to adjust the rotational angles and torque associated with the rotary driving in the joint sections 421a to 421f. Further, the actuator of the joint sections 421a to 421f is configured to be able to arbitrarily adjust a viscous drag coefficient on a rotary motion. For example, it is possible to implement a state in which rotation is easily performed (that is, the arm section 420 is easily moved by a manual motion) by force applied from the outside or a state in which rotation is not easily performed (that is, the arm section 420 is not easily moved by a manual motion) by force applied from the outside.

Referring to FIG. 3, an actuator 430 of the joint sections 421a to 421f according to the present embodiment includes a motor 424, a motor driver 425, a reduction gear 426, an encoder 427, a torque sensor 428, and a driving shaft 429. As illustrated in FIG. 3, the encoder 427, the motor 424, the reduction gear 426, and the torque sensor 428 are coupled to the driving shaft 429 in series in the described order.

The motor 424 is a prime mover in the actuator 430, and causes the driving shaft 429 to rotate about its axis. For example, the motor 424 is an electric motor such as a brushless DC motor. In the present embodiment, as the motor 424 is supplied with an electric current, the rotary driving is controlled.

The motor driver 425 is a driver circuit (a driver integrated circuit (IC)) for supplying an electric current to the motor 424 and rotationally driving the motor 424, and can control the number of revolutions of the motor 424 by adjusting an amount of electric current supplied to the motor 424. Further, the motor driver 425 can adjust the viscous drag coefficient on the rotary motion of the actuator 430 by adjusting an amount of electric current supplied to the motor 424.

The reduction gear 426 is connected to the driving shaft 429, and generates rotary driving force (that is, torque) having a certain value by reducing the rotation speed of the driving shaft 429 generated by the motor 424 at a certain reduction ratio. A high-performance reduction gear of a backlashless type is used as the reduction gear 426. For example, the reduction gear 426 may be a Harmonic Drive (a registered trademark). The torque generated by the reduction gear 426 is transferred to an output member (not illustrated) (for example, a coupling member of the links 422a to 422c, the imaging unit 423, or the like) at a subsequent stage through the torque sensor 428 connected to an output shaft of the reduction gear 426.

The encoder 427 is connected to the driving shaft 429, and detects the number of revolutions of the driving shaft 429.

It is possible to obtain information such as the rotational angle, the rotational angular velocity, and the rotational angular acceleration of the joint sections 421a to 421f on the basis of a relation between the number of revolutions of the driving shaft 429 detected by the encoder and the reduction ratio of the reduction gear 426.

The torque sensor 428 is connected to the output shaft of the reduction gear 426, and detects the torque generated by the reduction gear 426, that is, the torque output by the actuator 430. In the following description, the torque output by the actuator 430 is also referred to simply as "generated torque."

As described above, the actuator 430 can adjust the number of revolutions of the motor 424 by adjusting an amount of electric current supplied to the motor 424. Here, the reduction ratio of the reduction gear 426 may be appropriately set according to the purpose of the supporting arm apparatus 400. Thus, the generated torque can be controlled by appropriately adjusting the number of revolutions of the motor 424 according to the reduction ratio of the reduction gear 426. Further, in the actuator 430, it is possible to obtain information such as the rotational angle, the rotational angular velocity, and the rotational angular acceleration of the joint sections 421a to 421f on the basis of the number of revolutions of the driving shaft 429 detected by the encoder 427, and it is possible to detect the generated torque in the joint sections 421a to 421f through the torque sensor 428.

Further, the torque sensor 428 can detect external torque applied from the outside as well as the generated torque generated by the actuator 430. Thus, as the motor driver 425 adjusts an amount of electric current supplied to the motor 424 on the basis of the external torque detected by the torque sensor 428, it is possible to adjust the viscous drag coefficient on the rotary motion and implement, for example, the state in which rotation is easily or not easily performed by force applied from the outside.

Figure 4A:
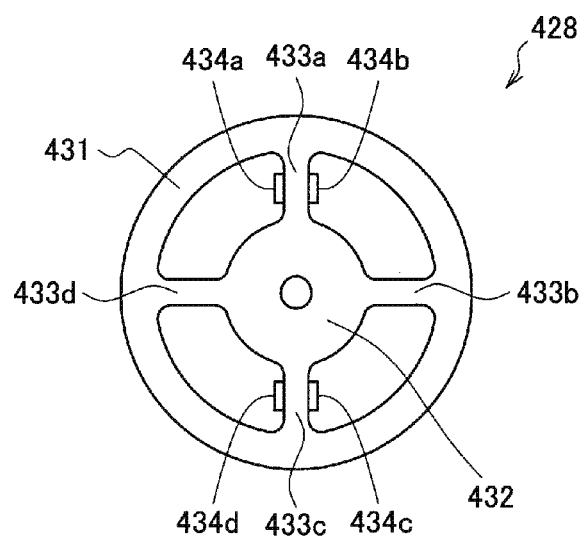
FIG. 4A is a schematic diagram schematically illustrating a state of a torque sensor illustrated in FIG. 3 viewed in an axis direction of a driving shaft.

Here, a configuration of the torque sensor 428 will be described in detail with reference to FIGS. 4A and 4B. FIG. 4A is a schematic diagram schematically illustrating a state of the torque sensor 428 illustrated in FIG. 3 viewed in the axis direction of the driving shaft 429.

Referring to FIG. 4A, the torque sensor 428 includes an outer ring section 431, an inner ring section 432, beam sections 433a to 433d, and distortion detecting elements 434a to 434d. As illustrated in FIG. 4A, the outer ring section 431 and the inner ring section 432 are concentrically arranged. In the present embodiment, the inner ring section 432 is connected to an input side, that is, the output shaft of the reduction gear 426, and the outer ring section 431 is connected to an output side, that is, an output member (not illustrated) at a subsequent stage.

The 4 beam sections 433a to 433d are arranged between the outer ring section 431 and the inner ring section 432 that are concentrically arranged, and connect the outer ring section 431 with the inner ring section 432. As illustrated in FIG. 4A, the beam sections 433a to 433d are interposed between the outer ring section 431 and the inner ring section 432 so that two neighboring sections of the beam sections 433a to 433d form an angle of 90 degree.

The distortion detecting elements 434a to 434d are installed at the two sections facing each other, that is, disposed at an angle of 180 degree among the beam sections 433a to 433d. It is possible to detect the generated torque and the external torque of the actuator 430 on the basis of a deformation amount of the beam sections 433a to 433d detected by the distortion detecting elements 434a to 434d.

In the example illustrated in FIG. 4A, among the beam sections 433a to 433d, the distortion detecting elements 434a and 434b are installed at the beam section 433a, and the distortion detecting elements 434c and 434d are installed at the beam section 433c. Further, the distortion detecting elements 434a and 434b are installed with the beam section 433a interposed therebetween, and the distortion detecting elements 434c and 434d are installed with the beam section 433c interposed therebetween. For example, the distortion detecting elements 434a to 434d are distortion gauges attached to the surfaces of the beam sections 433a and 433c, and detect geometric deformation amounts of the beam sections 433a and 433c on the basis of a change in electrical resistance. As illustrated in FIG. 4A, the distortion detecting elements 434a to 434d are installed at 4 positions, and the detecting elements 434a to 434d configure a so-called Wheatstone bridge. Thus, since it is possible to detect distortion using a so-called four-gauge technique, it is possible to reduce influence of interference of shafts other than a shaft in which distortion is detected, eccentricity of the driving shaft 429, a temperature drift, or the like.

As described above, the beam sections 433a to 433d serve as a distortion inducing body whose distortion is detected. The type of the distortion detecting elements 434a to 434d according to the present embodiment is not limited to a distortion gauge, and any other element may be used. For example, the distortion detecting elements 434a to 434d may be elements that detect the deformation amounts of the beam sections 433a to 433d on the basis of a change in magnetic characteristics.

Further, although not illustrated in FIGS. 3 and 4A, the following configuration may be applied in order to improve the detection accuracy of the generated torque and the external torque by the torque sensor 428. For example, when portions of the beam sections 433a to 433d which are connected with the outer ring section 431 are formed at a thinner thickness than other portions, since a support moment is released, linearity of a deformation amount to be detected is improved, and influence by a radial load is reduced. Further, when both the outer ring section 431 and the inner ring section 432 are supported by a housing through a bearing, it is possible to exclude an action of other axial force and a moment from both the input shaft and the output shaft. Further, in order to reduce another axial moment acting on the outer ring section 431, a support bearing may be arranged at the other end of the actuator 430 illustrated in FIG. 3, that is, a portion at which the encoder 427 is arranged.

The configuration of the torque sensor 428 has been described above with reference to FIG. 4A. As described above, through the configuration of the torque sensor 428 illustrated in FIG. 4A, it is possible to detect the generated torque and the external torque of the actuator 430 with a high degree of accuracy.

Here, in the present embodiment, the configuration of the torque sensor 428 is not limited to the configuration illustrated in FIG. 4A and may be any other configuration. Another exemplary configuration of the torque sensor applied to the actuator 430 other than the torque sensor 428 will be described with reference to FIG. 4B.

Figure 4B:
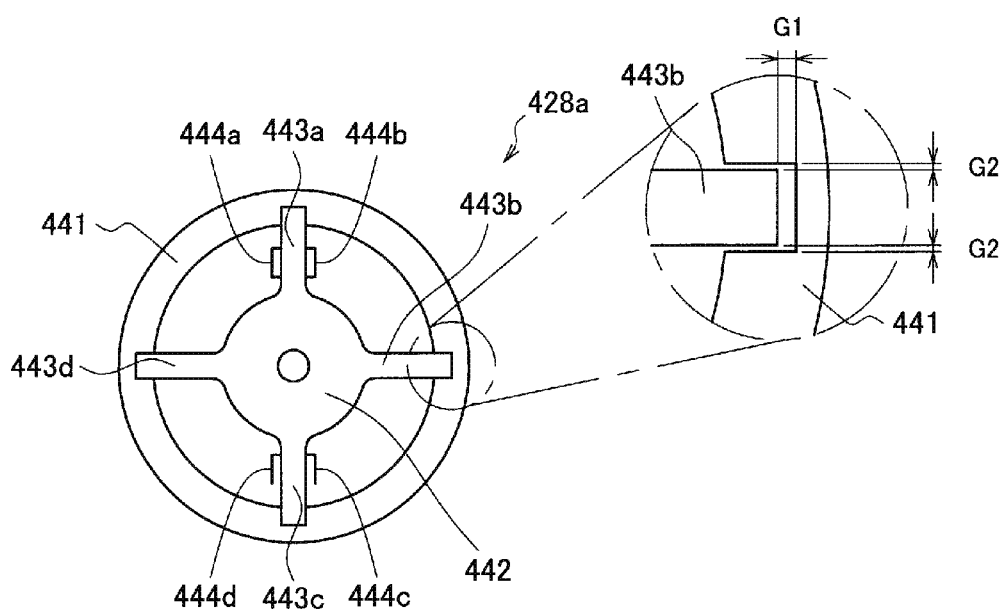
FIG. 4B is a schematic diagram illustrating another exemplary configuration of a torque sensor applied to the actuator illustrated in FIG. 3.

FIG. 4B is a schematic diagram illustrating another exemplary configuration of the torque sensor applied to the actuator 430 illustrated in FIG. 3. Referring to FIG. 4B, a torque sensor 428a according to the present modified example includes an outer ring section 441, an inner ring section 442, beam sections 443a to 443d, and distortion detecting elements 444a to 444d. Note that FIG. 4B schematically illustrates a state of the torque sensor 428a viewed in the axis direction of the driving shaft 429, similarly to FIG. 4A.

In the torque sensor 428a, functions and configurations of the outer ring section 441, the inner ring section 442, the beam sections 443a to 443d, and the distortion detecting elements 444a to 444d are similar to the functions and the configurations of the outer ring section 431, the inner ring section 432, the beam sections 433a to 433d, and the distortion detecting elements 434a to 434d of the torque sensor 428 described above with reference to FIG. 4A. The torque sensor 428a according to the present modified example differs in a configuration of a connection portion of the beam sections 443a to 443d and the outer ring section 441. Thus, the torque sensor 428a illustrated in FIG. 4B will be described focusing on a configuration of the connection portion of the beam sections 443a to 443d and the outer ring section 441 that is the difference with the torque sensor 428 illustrated in FIG. 4A, and a description of a duplicated configuration will be omitted.

Referring to FIG. 4B, the connection portion of the beam section 443b and the outer ring section 441 is enlarged and illustrated together with a general view of the torque sensor 428a. Note that, in FIG. 4B, only the connection portion of the beam section 443b and the outer ring section 441 which is one of the four connection portions of the beam sections 443a to 443d and the outer ring section 441 is enlarged and illustrated, but the other 3 connection portions of the beam sections 443a, 443c, and 443d and the outer ring section 441 have the same configuration.

Referring to an enlarged view in FIG. 4B, in the connection portion of the beam section 443b and the outer ring section 441, an engagement concave portion is formed in the outer ring section 441, and the beam section 443b is connected with the outer ring section 441 such that the front edge of the beam section 443b is engaged with the engagement concave portion. Further, gaps G1 and G2 are formed between the beam section 443b and the outer ring section 441. The gap G1 indicates a gap between the beam section 443b and the outer ring section 441 in a direction in which the beam section 443b extends toward the outer ring section 441, and the gap G2 indicates a gap between the beam section 443b and the outer ring section 441 in a direction orthogonal to that direction.

As described above, in the torque sensor 428a, the beam sections 443a to 443d and the outer ring section 441 are arranged to be separated from each other with the certain gaps G1 and G2. In other words, in the torque sensor 428a, the outer ring section 441 is separated from the inner ring section 442. Thus, since the inner ring section 442 has a degree of freedom of a motion without being bound to the outer ring section 441, for example, even when vibration occurs at the time of driving of the actuator 430, a distortion by vibration can be absorbed by the air gaps G1 and G2 between the inner ring section 442 and the outer ring section 441. Thus, as the torque sensor 428a is applied as the torque sensor of the actuator 430, the generated torque and the external torque are detected with a high degree of accuracy.

Note that JP 2009-269102A and JP 2011-209099A which are patent applications previously filed by the present applicant, for example, can be referred to for the configuration of the actuator 430 corresponding to the ideal joint control illustrated in FIGS. 3, 4A, and 4B.

The schematic configuration of the supporting arm apparatus 400 according to the present embodiment has been described above with reference to FIGS. 2, 3, 4A, and 4B. Next, the whole body cooperative control and the ideal joint control for controlling driving of the arm section 420, that is, driving of the joint sections 421a to 421f in the supporting arm apparatus 400 according to the present embodiment, will be described.

2-2. Generalized Inverse Dynamics

Next, an overview of the generalized inverse dynamics used for the whole body cooperative control of the supporting arm apparatus 400 according to the present embodiment will be described.

The generalized inverse dynamics are basic operations in whole body cooperative control of a multi-link structure of converting purposes of motion related to various dimensions in various kinds of operation spaces into torque to be generated by a plurality of joint sections in view of various kinds of constraint conditions in a multi-link structure (for example, the arm section 420 illustrated in FIG. 2 in the present embodiment) configured such that a plurality of links are coupled by a plurality of joint sections.

The operation space is an important concept in the force control of the robot apparatus. The operation space is a space for describing a relation between force acting on the multi-link structure and acceleration of the multi-link structure. When the driving control of the multi-link structure is performed by the force control rather than the position control, the concept of the operation space is necessary in the case in which a way of dealing with the multi-link structure and the environment is used as a constraint condition. The operation space is, for example, a space to which the multi-link structure belongs such as a joint space, a Cartesian space, or a momentum space.

The purpose of motion indicates a target value in the driving control of the multi-link structure, and, for example, a target value of a position, a speed, acceleration, force, or an impedance of the multi-link structure that is desired to be achieved through the driving control.

The constraint condition is a constraint condition related to, for example, a position, a speed, acceleration, or force of the multi-link structure that is decided by the shape or the structure of the multi-link structure, the environment around the multi-link structure, a setting performed by the user, or the like. For example, the constraint condition includes information about generated force, a priority, the presence or absence of a non-driven joint, vertical reactive force, a friction cone, a support polygon, and the like.

In the generalized dynamics, in order to achieve both stability of numeric calculation and real-time processable operation efficiency, an operation algorithm includes a virtual force decision process (a virtual force calculating process) serving as a first stage and an actual force conversion process (an actual force calculating process) serving as a second stage. In the virtual force calculating process serving as the first stage, virtual force serving as virtual force that is necessary for achieving each purpose of motion and acts on the operation space is decided in view of a priority of a purpose of motion and a maximum value of the virtual force. In the actual force calculating process serving as the second stage, the calculated virtual force is converted into actual force that can be implemented by a configuration of an actual multi-link structure such as joint force or external force in view of a constraint related to a non-driven joint, vertical reactive force, a friction cone, a support polygon, or the like. The virtual force calculating process and the actual force calculating process will be described below. Note that, in the following description of the virtual force calculating process, the actual force calculating process, and the ideal joint control, for easier understanding, there are cases in which an exemplary configuration of the arm section 420 of the supporting arm apparatus 400 according to the present embodiment illustrated in FIGS. 2 and 3 is described as a specific example.

2-2-1. Virtual Force Calculating Process

A vector including certain physical quantities in the joint sections of the multi-link structure is referred to as a "generalized variable q" (also referred to as a "joint value q" or a "joint space q"). An operation space x is defined by the following Equation (1) using a time differential value of the generalized variable q and a Jacobian J:

[Math. 1]

$$\dot{x} = J\dot{q} \quad (1)$$

In the present embodiment, for example, q indicates a rotational angle in the joint sections 421a to 421f of the arm section 420. An equation of motion related to the operation space x is described by the following Equation (2):

[Math. 2]

$$\ddot{x} = \Lambda^{-1} f + c \quad (2)$$

Here, f indicates force acting on the operation space x. Further, $\Lambda^{-1}$ indicates an operation space inertia inverse matrix, c indicates operation space bias acceleration, and $\Lambda^{-1}$ and c are expressed by the following Equations (3) and (4).

[Math. 3]

$$\Lambda^{-1} = JH^{-1}J^T \quad (3)$$

$$c = JH^{-1}(\tau - b) + \dot{J}\dot{q} \quad (4)$$

Note that H indicates a joint space inertia matrix, τ indicates joint force (for example, generated torque in the joint sections 421a to 421f) corresponding to the joint value q, and b is a term indicating gravity, Coriolis force, or centrifugal force.

In the generalized inverse dynamics, the purpose of motion of the position and the speed related to the operation space x is known to be expressed as acceleration of the operation space x. At this time, in order to implement the operation space acceleration serving as the target value given as the purpose of motion from Equation (1), virtual force $f_v$ that has to act on the operation space x is obtained by solving a sort of linear complementary problem (LCP) expressed by the following Equation (5).

[Math. 4]

$$w + \ddot{x} = \Lambda^{-1} f_v + c \quad (5)$$

$$\text{s.t.} \begin{cases} ((w_i < 0) \cap (f_{v_i} = U_i)) \cup \\ ((w_i > 0) \cap (f_{v_i} = L_i)) \cup \\ ((w_i = 0) \cap (L_i < f_{v_i} < U_i)) \end{cases}$$

Here, $L_i$ and $U_i$ are set to a negative lower limit value (including $-\infty$) of an i-th component of $f_v$ and a positive upper limit value (including $+\infty$) of the i-th component of $f_v$. The LCP can be solved, for example, using an iterative technique, a pivot technique, a method using robust acceleration control, or the like.

Note that the operation space inertia inverse matrix $\Lambda^{-1}$ and the bias acceleration c are large in a calculation cost when they are calculated as in Equations (3) and (4) serving as definitional equations. Thus, a method of performing the calculation process of the operation space inertia inverse matrix $\Lambda^{-1}$ at a high speed by applying a forward dynamics calculation (FWD) of calculating generalized acceleration (joint acceleration) from generalized force (the joint force τ) of the multi-link structure has been proposed. Specifically, the operation space inertia inverse matrix $\Lambda^{-1}$ and the bias acceleration c can be obtained on the basis of information related to force acting on the multi-link structure (for example, the arm section 420 and the joint sections 421a to 421f) such as the joint space q, the joint force τ, or the gravity g using the forward dynamics calculation FWD. As described above, the operation space inertia inverse matrix $\Lambda^{-1}$ can be calculated with a calculation amount of O (N) on the number N of joint sections by applying the forward dynamics calculation FWD related to the operation space.

Here, as a setting example of the purpose of motion, a condition for achieving the target value (indicated by adding a bar above a second order differential of x) of the operation space acceleration by the virtual force $f_{v_i}$ of an absolute value $F_i$ or less can be expressed by the following Equation (6):

[Math. 5]

$$L_i = -F_i,$$

$$U_i = F_i,$$

$$\ddot{x}_i = \bar{\ddot{x}}_i \quad (6)$$

Further, as described above, the purpose of motion related to the position and the speed of the operation space x can be represented as the target value of the operation space acceleration and is specifically expressed by the following Equation (7) (the target value of the position and the speed of the operation space x are indicated by adding a bar above x and a first order differential of x).

[Math. 6]

$$\bar{\ddot{x}}_i = K_p(\bar{x}_i - x_i) + K_v(\bar{\dot{x}}_i - \dot{x}_i) \quad (7)$$

It is also possible to set the purpose of motion related to the operation space (momentum, Cartesian relative coordinates, an interlocked joint, and the like) represented by a linear sum of other operation spaces using an approach of a decomposition operation space. Note that it is necessary to give priorities to competing purposes of motion. The LCP is solved for each priority or in ascending order of priorities, and it is possible to cause virtual force obtained from a previous LCP to act as known external force of a subsequent LCP.

2-2-2. Actual Force Calculating Process

In the actual force calculating process serving as the second stage of the generalized inverse dynamics, a process of replacing the virtual force $f_v$ obtained in (2-2-1. Virtual force decision process) with actual joint force and external force is performed. A condition of implementing generalized force $\tau_v = J_v^T f_v$ based on virtual force through generated torque $\tau_a$ generated by the joint section and external force $f_e$ is expressed by the following Equation (8).

[Math. 7]

$$\begin{bmatrix} J_{vu}^T \\ J_{va}^T \end{bmatrix}(f_v - \Delta f_v) = \begin{bmatrix} J_{eu}^T \\ J_{ea}^T \end{bmatrix} f_e + \begin{bmatrix} 0 \\ \tau_a \end{bmatrix} \quad (8)$$

Here, a subscript a indicates a set of driven joint sections (a driven joint set), and a subscript u indicates a set of non-driven joint sections (a non-driven joint set). In other words, the upper portions in Equation (8) represent balance of force of a space (a non-driven joint space) by the non-driven joint section, and the lower portions represent balance of force of a space (a driven joint space) by the driven joint section. $J_{vu}$ and $J_{va}$ indicate a non-driven joint component and a driven joint component of a Jacobian related to the operation space on which the virtual force $f_v$ acts, respectively. $J_{eu}$ and $J_{ea}$ indicate a non-driven joint component and a driven joint component of a Jacobian related to the operation space on which the external force $f_e$ acts. $\Delta f_v$ indicates a component of the virtual force $f_v$ that is hardly implemented by actual force.

The upper portions in Equation (8) are undefined, and, for example, $f_e$ and $\Delta f_v$ can be obtained by solving a quadratic programming problem (QP) expressed by the following Equation (9).

[Math. 8]

$$\min \tfrac{1}{2}\varepsilon^T Q_1 \varepsilon + \tfrac{1}{2}\xi^T Q_2 \xi$$

$$s \cdot t \cdot U \xi \geq v \quad (9)$$

Here, $\varepsilon$ is a difference between sides of the upper portions in Equation (8), and indicates an equation error. $\xi$ is a coupling vector of $f_e$ and $\Delta f_v$, and indicates a variable vector. $Q_1$ and $Q_2$ are positive definite symmetric matrices indicating weights at the time of minimization. Further, an inequality constraint of Equation (9) is used to express a constraint condition related to external force such as vertical reactive force, a friction cone, a maximum value of external force, and a support polygon. For example, an inequality constraint related to a rectangular support polygon is expressed by the following Equation (10).

[Math. 9]

$$|F_x| \leq \mu_t F_z,$$

$$|F_y| \leq \mu_t F_z,$$

$$F_z \geq 0,$$

$$|M_x| \leq d_y F_z,$$

$$|M_y| \leq d_x F_z,$$

$$|M_z| \leq \mu_r F_z \quad (10)$$

Here, z indicates a normal direction of a contact surface, and x and y indicate two orthogonal tangential directions that are vertical to z. $(F_x, F_y, F_z)$ and $(M_x, M_y, M_z)$ are external force and external force moment acting on a contact point. $\mu_t$ and $\mu_r$ indicate friction coefficients related to translation and rotation. $(d_x, d_y)$ indicates a size of a support polygon.

The solutions $f_e$ and $\Delta f_v$ of a minimum norm or a minimum error are obtained from Equations (9) and (10). It is possible to obtain the joint force $\tau_a$ necessary for implementing the purpose of motion by substituting $f_e$ and $\Delta f_v$ obtained from Equation (9) into the lower portion of Equation (8).

In the case of a system in which the basis is fixed, and there is no non-driven joint, all virtual force can be replaced only with joint force, and $f_e=0$ and $\Delta f_v=0$ can be set in Equation (8). In this case, the following Equation (11) can be obtained for the joint force $\tau_a$ from the lower portions in Equation (8).

[Math. 10]

$$\tau_a = J_{va}^T f_v \quad (11)$$

The whole body cooperative control using the generalized inverse dynamics according to the present embodiment has been described above. As described above, as the virtual force calculating process and the actual force calculating process are sequentially performed, it is possible to obtain the joint force $\tau_a$ for achieving a desired purpose of motion. In other words, conversely, as the calculated joint force $\tau_a$ is reflected in a theoretical model in motion of the joint sections 421a to 421f, the joint sections 421a to 421f are driven to achieve a desired purpose of motion.

Note that JP 2009-95959A and JP 2010-188471A which are patent applications previously filed by the present applicant, for example, can be referred to for the whole body cooperative control using the generalized inverse dynamics described above, particularly, for the details of a process of deriving the virtual force $f_v$, a method of solving the LCP and obtaining the virtual force $f_v$, the resolution to the QP problem, and the like.

2-3. Ideal Joint Control

Next, the ideal joint control according to the present embodiment will be described. Motion of each of the joint sections 421a to 421f is modelized by an equation of motion of a second order delay system of the following Equation (12):

[Math. 11]

$$I_a \ddot{q} = \tau_a + \tau_e - \nu_a \dot{q} \quad (12)$$

Here, $I_a$ indicates an inertia moment (inertia) in a joint section, $\tau_a$ indicates generated torque of the joint sections 421a to 421f, $\tau_e$ indicates external torque acting on each of the joint sections 421a to 421f, and $\nu_a$ indicates a viscous drag coefficient in each of the joint sections 421a to 421f. Equation (12) can also be regarded as a theoretical model representing motion of the actuator 430 in the joint sections 421a to 421f.

As described above in [2-2. Generalized inverse dynamics], through the calculation using the generalized inverse dynamics, it is possible to calculate $\tau_a$ serving as actual force that each of the joint sections 421a to 421f has to use to implement the purpose of motion using the purpose of motion and the constraint condition. Thus, ideally, a response according to the theoretical model expressed by Equation (12) is implemented, that is, a desired purpose of motion is achieved by applying each calculated $\tau_a$ to Equation (12).

However, practically, there are cases in which an error (a modelization error) between motion of the joint sections 421a to 421f and the theoretical model expressed by Equation (12) occurs due to influence of various disturbances. The modelization error is classified into an error caused by a mass property such as a weight, a center of gravity, or a tensor of inertia of the multi-link structure and an error caused by friction, inertia, or the like in the joint sections 421a to 421f. Of these, the modelization error of the former caused by the mass property can be relatively easily reduced at the time of construction of the theoretical model by applying high-accuracy computer aided design (CAD) data or an identification method.

Meanwhile, the modelization error of the latter caused by friction, inertia, or the like in the joint sections 421a to 421f occurs due to a phenomenon that it is difficult to modelize, for example, friction or the like in the reduction gear 426 of the joint sections 421a to 421f, and an unignorable modelization error may remain at the time of construction of the theoretical model. Further, there is likely to be an error between a value of an inertia $I_a$ or a viscous drag coefficient $v_e$ in Equation (12) and an actual value in the joint sections 421a to 421f. The error that is hardly modeled may act as a disturbance in the driving control of the joint sections 421a to 421f. Thus, due to influence of such a disturbance, practically, there are cases in which motion of the joint sections 421a to 421f does not respond as in the theoretical model expressed by Equation (12). Thus, there are cases in which it is difficult to achieve the purpose of motion of the control target even when the actual force $\tau_a$ serving as the joint force calculated by the generalized inverse dynamics is applied. In the present embodiment, an active control system is added to each of the joint sections 421a to 421f, and thus the response of the joint sections 421a to 421f is considered to be corrected such that an ideal response according to the theoretical model expressed by Equation (12) is performed. Specifically, in the present embodiment, torque control of a friction compensation type using the torque sensors 428 and 428a of the joint sections 421a to 421f is performed, and in addition, it is possible to perform an ideal response according to an ideal value even on the inertia $I_a$ and the viscous drag coefficient $v_a$ for the requested generated torque $\tau_a$ and the requested external torque $\tau_e$.

In the present embodiment, controlling driving of the joint section such that the joint sections 421a to 421f of the supporting arm apparatus 400 perform the ideal response expressed by Equation (12) is referred to as the ideal joint control as described above. Here, in the following description, an actuator whose driving is controlled by the ideal joint control is also referred to as a "virtualized actuator (VA)" since the ideal response is performed. The ideal joint control according to the present embodiment will be described below with reference to FIG. 5.

Figure 5:
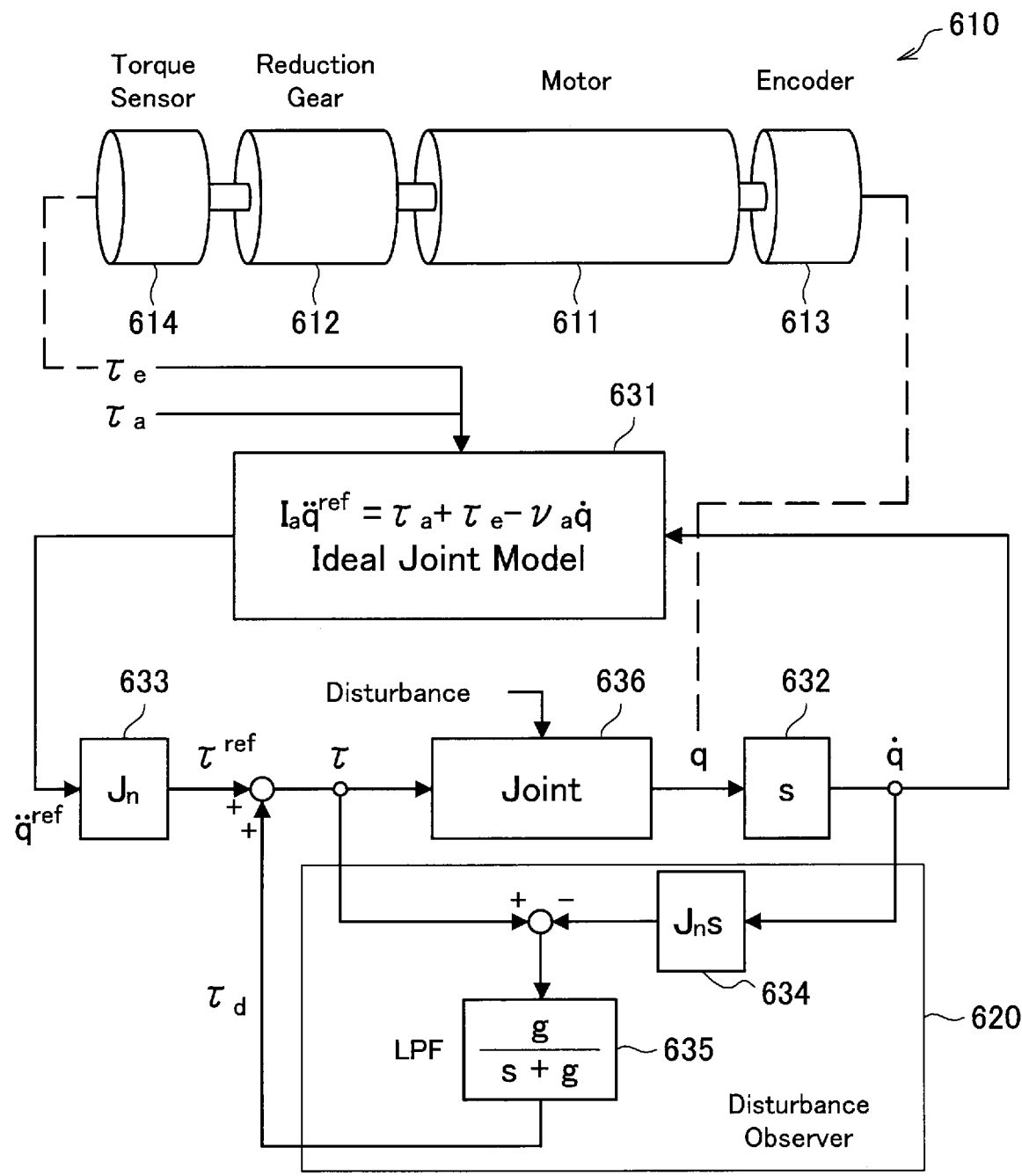
FIG. 5 is an explanatory diagram for describing ideal joint control according to an embodiment of the present disclosure.

FIG. 5 is an explanatory diagram for describing the ideal joint control according to an embodiment of the present disclosure. FIG. 5 schematically illustrates a conceptual computing device that performs various kinds of operations according to the ideal joint control using blocks.

Referring to FIG. 5, an actuator 610 schematically illustrates a mechanism of the actuator 430 illustrated in FIG. 3, and a motor 611, a reduction gear 612, an encoder 613, and a torque sensor 614 correspond to the motor 424, the reduction gear 426, the encoder 427, and the torque sensor 428 (or the torque sensor 428a illustrated in FIG. 4B) which are illustrated in FIG. 3.

Here, when the actuator 610 performs the response according to the theoretical model expressed by Equation (12), it means that the rotational angular acceleration at the left side is achieved when the right side of Equation (12) is given. Further, as expressed in Equation (12), the theoretical model includes an external torque term $\tau_e$ acting on the actuator 610. In the present embodiment, in order to perform the ideal joint control, the external torque $\tau_e$ is measured by the torque sensor 614. Further, a disturbance observer 620 is applied to calculate a disturbance estimation value $\tau_d$ serving as an estimation value of torque caused by a disturbance based on a rotational angle q of the actuator 610 measured by the encoder 613.

A block 631 represents a computing device that performs an operation according to the ideal joint model of the joint sections 421a to 421f expressed by Equation (12). The block 631 can receive the generated torque $\tau_a$, the external torque $\tau_e$, and the rotational angular velocity (the first order differential of the rotational angle q) and output the rotational angular acceleration target value (a second order differential of a rotational angle target value $q^{ref}$) shown at the left side of Equation (12).

In the present embodiment, the generated torque $\tau_a$ calculated by the method described in [2-2. Generalized inverse dynamics] and the external torque $\tau_e$ measured by the torque sensor 614 are input to the block 631. Meanwhile, the rotational angle q measured by the encoder 613 is input to a block 632 indicating a computing device that performs differential operation, and thus the rotational angular velocity (the first order differential of the rotational angle q) is calculated. In addition to the generated torque $\tau_a$ and the external torque $\tau_e$, the rotational angular velocity calculated by the block 632 is input to the block 631, and thus the rotational angular acceleration target value is calculated by the block 631. The calculated rotational angular acceleration target value is input to a block 633.

The block 633 indicates a computing device that calculates torque to be generated in the actuator 610 on the basis of the rotational angular acceleration of the actuator 610. In the present embodiment, specifically, the block 633 can obtain a torque target value $\tau^{ref}$ by multiplying a nominal inertia $J_n$ of the actuator 610 to the rotational angular acceleration target value. In the ideal response, a desired purpose of motion is achieved by causing the actuator 610 to generate the torque target value $\tau^{ref}$, but there are cases in which an actual response is influenced by a disturbance or the like as described above. Thus, in the present embodiment, the disturbance estimation value $\tau_d$ is calculated by the disturbance observer 620, and the torque target value $\tau^{ref}$ is corrected using the disturbance estimation value $\tau_d$.

A configuration of the disturbance observer 620 will be described. As illustrated in FIG. 5, the disturbance observer 620 calculates the disturbance estimation value $\tau_d$ on the basis of a torque command value $\tau$ and the rotational angular velocity calculated from the rotational angle q measured by the encoder 613. Here, the torque command value $\tau$ is a torque value to be finally generated by the actuator 610 after influence of the disturbance is corrected. For example, when no disturbance estimation value $\tau_d$ is calculated, the torque command value $\tau$ is used as the torque target value $\tau^{ref}$.

The disturbance observer 620 includes a block 634 and a block 635. The block 634 is a computing device that calculates torque to be generated by the actuator 610 on the basis of the rotational angular velocity of the actuator 610. In the present embodiment, specifically, the rotational angular velocity calculated by the block 632 on the basis of the rotational angle q measured by the encoder 613 is input to the block 634. The block 634 can obtain the rotational angular acceleration by performing an operation expressed by a transfer function Ls, that is, by differentiating the rotational angular velocity, and calculate an estimation value (a torque estimation value) of torque actually acting on the actuator 610 by multiplying the calculated rotational angular acceleration by the nominal inertia $J_n$.

In the disturbance observer 620, a difference between the torque estimation value and the torque command value τ is obtained, and thus the disturbance estimation value $\tau_d$ serving as a value of torque by a disturbance is estimated. Specifically, the disturbance estimation value $\tau_d$ may be a difference between the torque command value τ in the previous control and the torque estimation value in the current control. Since the torque estimation value calculated by the block 634 is based on an actual measurement value, and the torque command value τ calculated by the block 633 is based on the ideal theoretical model of the joint sections 421a to 421f indicated by the block 631, it is possible to estimate influence of a disturbance that is not considered in the theoretical model by obtaining the difference of the two values.

In addition, the disturbance observer 620 is further provided with a low pass filter (LPF) indicated by the block 635 in order to prevent a divergence of a system. The block 635 performs an operation represented by a transfer function g/(s+g), outputs only a low frequency component in response to an input value, and stabilizes a system. In the present embodiment, a difference value between the torque estimation value calculated by the block 634 and the torque command value $\tau^{ref}$ is input to the block 635, and the low frequency component is calculated as the disturbance estimation value $\tau_d$.

In the present embodiment, feedforward control of adding the disturbance estimation value $\tau_d$ calculated by the disturbance observer 620 to the torque target value $\tau^{ref}$ is performed, and thus the torque command value τ serving as a torque value to be finally generated by the actuator 610 is calculated. Then, the actuator 610 is driven on the basis of the torque command value τ. Specifically, the torque command value τ is converted into a corresponding electric current value (an electric current command value), the electric current command value is applied to the motor 611, so that the actuator 610 is driven.

By employing the configuration described above with reference to FIG. 5, in the driving control of the joint sections 421a to 421f according to the present embodiment, even when there is a disturbance component such as friction, it is possible for the response of the actuator 610 to follow the target value. Further, it is possible to perform the ideal response according to the inertia $I_a$ and the viscous drag coefficient $v_a$ assumed by the theoretical model in the driving control of the joint sections 421a to 421f.

Note that, JP 2009-269102A that is a patent application previously filed by the present applicant, for example, can be referred to for the details of the above-described ideal joint control.

The ideal joint control according to the present embodiment has been described above with reference to FIG. 5 together with the generalized inverse dynamics used in the present embodiment. As described above, in the present embodiment, the whole body cooperative control of calculating driving parameters (for example, the generated torque values of the joint sections 421a to 421f) of the joint sections 421a to 421f for achieving the purpose of motion of the arm section 420 is performed in view of the constraint condition using the generalized inverse dynamics. Further, as described above with reference to FIG. 5, in the present embodiment, as correction in which influence of a disturbance is considered is performed on the generated torque value calculated by the whole body cooperative control using the generalized inverse dynamics, the ideal joint control of implementing the ideal response based on the theoretical model in the driving control of the joint sections 421a to 421f is performed. Thus, in the present embodiment, it is possible to perform high-accuracy driving control for achieving the purpose of motion for driving of the arm section 420.

2-4. Configuration of Supporting Arm Control System

Next, a configuration of the supporting arm control system according to the present embodiment in which the whole body cooperative control and the ideal joint control described in [2-2. Generalized inverse dynamics] and [2-3. Ideal joint control] are applied to the driving control of the supporting arm apparatus will be described.

Figure 6:
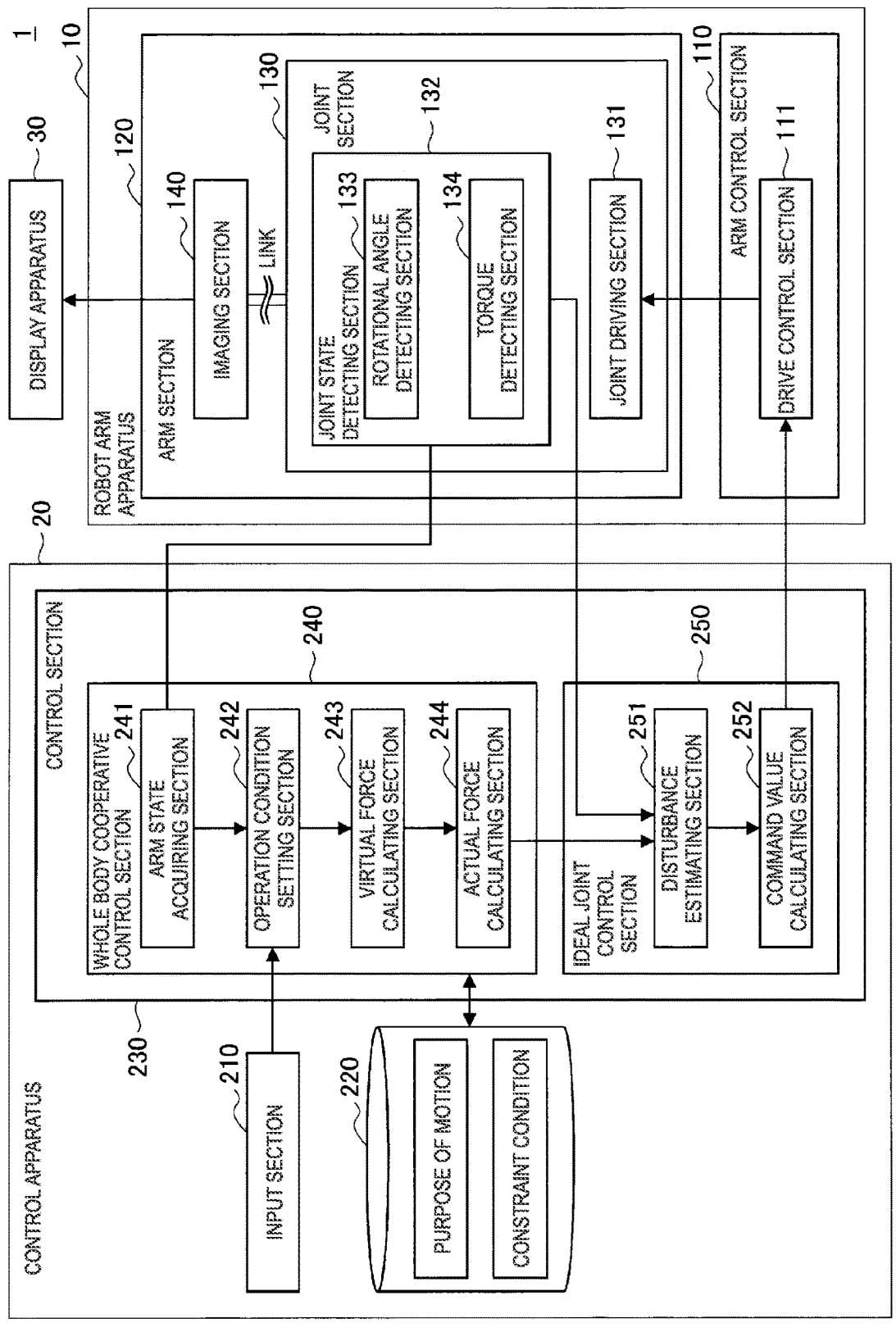
FIG. 6 is a functional block diagram illustrating an exemplary configuration of a supporting arm control system according to an embodiment of the present disclosure.

An exemplary configuration of the supporting arm control system according to an embodiment of the present disclosure will be described with reference to FIG. 6. FIG. 6 is a functional block diagram illustrating an exemplary configuration of the supporting arm control system according to an embodiment of the present disclosure. Note that, in the supporting arm control system illustrated in FIG. 6, components related to driving control of the arm section of the supporting arm apparatus are mainly illustrated.

Referring to FIG. 6, a supporting arm control system 1 according to an embodiment of the present disclosure includes a supporting arm apparatus 10, a control apparatus 20, and a display apparatus 30. In the present embodiment, various kinds of operations in the whole body cooperative control described in [2-2. Generalized inverse dynamics] and the ideal joint control described in [2-3. Ideal joint control] through the control apparatus 20 are performed, and driving of the arm section of the supporting arm apparatus 10 is controlled on the basis of the operation result. Further, the arm section of the supporting arm apparatus 10 is provided with an imaging section 140 which will be described later, and an image captured by the imaging section 140 is displayed on a display screen of the display apparatus 30. Next, configurations of the supporting arm apparatus 10, the control apparatus 20, and the display apparatus 30 will be described in detail.

The supporting arm apparatus 10 includes an arm section having a multi-link structure including a plurality of joint sections and a plurality of links, and drives the arm section in the movable region to control the position and posture of the front edge unit installed at the front edge of the arm section. The supporting arm apparatus 10 corresponds to the supporting arm apparatus 400 illustrated in FIG. 2.

Referring to FIG. 6, the supporting arm apparatus 10 includes an arm control section 110 and an arm section 120. The arm section 120 includes a joint section 130 and the imaging section 140.

The arm control section 110 controls the supporting arm apparatus 10 in an integrated manner, and controls driving of the arm section 120. The arm control section 110 corresponds to the control section (not illustrated in FIG. 2) described above with reference to FIG. 2. Specifically, the arm control section 110 includes a drive control section 111, and controls driving of the arm section 120, and driving of the arm section 120 is controlled by controlling driving of the joint section 130 according to control of the drive control section 111. More specifically, the drive control section 111 controls the number of revolutions of the motor in the actuator of the joint section 130 and the rotational angle and the generated torque of the joint section 130 by controlling an amount of electric current supplied to the motor. Here, as described above, driving control of the arm section 120 by the drive control section 111 is performed on the basis of the operation result in the control apparatus 20. Thus, an amount of electric current that is controlled by the drive control section 111 and supplied to the motor in the actuator of the joint section 130 is an amount of electric current decided on the basis of the operation result in the control apparatus 20.

The arm section 120 has a multi-link structure including a plurality of joint sections and a plurality of links, and driving of the arm section 120 is controlled according to control of the arm control section 110. The arm section 120 corresponds to the arm section 420 illustrated in FIG. 2. The arm section 120 includes the joint section 130 and the imaging section 140. Note that, since the plurality of joint sections of the arm section 120 have the same function and configuration, a configuration of one joint section 130 representing the plurality of joint sections is illustrated in FIG. 6.

The joint section 130 couples links to be rotatable in the arm section 120, and the rotary driving of the joint section 130 is controlled according to control of the arm control section 110 such that the arm section 120 is driven. The joint section 130 corresponds to the joint sections 421a to 421f illustrated in FIG. 2. Further, the joint section 130 includes an actuator, and the actuator has a configuration similar to, for example, the configuration illustrated in FIGS. 3, 4A, and 4B.

The joint section 130 includes a joint driving section 131 and a joint state detecting section 132.

The joint driving section 131 is a driving mechanism in the actuator of the joint section 130, and as the joint driving section 131 is driven, the joint section 130 is rotationally driven. The drive control section 111 controls driving of the joint driving section 131. For example, the joint driving section 131 is a component corresponding to the motor 424 and the motor driver 425 illustrated in FIG. 3, and driving the joint driving section 131 corresponds to the motor driver 425 driving the motor 424 with an amount of electric current according to a command given from the drive control section 111.

The joint state detecting section 132 detects the state of the joint section 130. Here, the state of the joint section 130 may mean a motion state of the joint section 130. For example, the state of the joint section 130 includes information such as the rotational angle, the rotational angular velocity, the rotational angular acceleration, and the generated torque of the joint section 130. In the present embodiment, the joint state detecting section 132 includes a rotational angle detecting section 133 that detects the rotational angle of the joint section 130 and a torque detecting section 134 that detects the generated torque and the external torque of the joint section 130. Note that the rotational angle detecting section 133 and the torque detecting section 134 correspond to the encoder 427 of the actuator 430 illustrated in FIG. 3 and the torque sensors 428 and 428a illustrated in FIGS. 4A and 4B. The joint state detecting section 132 transmits the detected state of the joint section 130 to the control apparatus 20.

The imaging section 140 is an example of the front edge unit installed at the front edge of the arm section 120, and acquires an image of a photographing target. The imaging section 140 corresponds to the imaging unit 423 illustrated in FIG. 2. Specifically, the imaging section 140 is, for example, a camera capable of photographing a photographing target in a moving image format or a still image format. More specifically, the imaging section 140 includes a plurality of light receiving elements arranged two dimensionally, and can perform photoelectric conversion in the light receiving elements and acquire an image signal indicating an image of a photographing target. The imaging section 140 transmits the acquired image signal to the display apparatus 30.

Note that, similarly to the supporting arm apparatus 400 of FIG. 2 in which the imaging unit 423 is installed at the front edge of the arm section 420, in the supporting arm apparatus 10, the imaging section 140 is actually installed at the front edge of the arm section 120. In FIG. 6, the form in which the imaging section 140 is installed at the front edge of the last link through the plurality of joint sections 130 and a plurality of links is represented by schematically illustrating the link between the joint section 130 and the imaging section 140.

Note that, in the present embodiment, various kinds of medical apparatuses may be connected to the front edge of the arm section 120 as the front edge unit. As the medical apparatus, for example, there are various kinds of units used when the medical procedure is performed such as various kinds of medical procedure instruments including a scalpel or forceps or one unit of various kinds of examination apparatuses including a probe of an ultrasonic examination apparatus. Further, in the present embodiment, the imaging section 140 illustrated in FIG. 6 or a unit having an imaging function such as an endoscope or a microscope may also be included as a medical apparatus. As described above, the supporting arm apparatus 10 according to the present embodiment may be a medical supporting arm apparatus including a medical apparatus. Similarly, the supporting arm control system 1 according to the present embodiment may be a medical supporting arm control system. Note that the supporting arm apparatus 10 illustrated in FIG. 6 will also be referred to as a VM supporting arm apparatus including a unit having an imaging function as a front edge unit. Further, a stereo camera including two imaging units (camera units) may be installed at the front edge of the arm section 120, and photography may be performed so that an imaging target is displayed as a 3D image.

The function and configuration of the supporting arm apparatus 10 have been described above. Next, a function and configuration of the control apparatus 20 will be described. Referring to FIG. 6, the control apparatus 20 includes an input section 210, a storage section 220, and a control section 230.

The control section 230 controls the control apparatus 20 in an integrated manner, and performs various kinds of operations for controlling driving of the arm section 120 in the supporting arm apparatus 10. Specifically, in order to control driving of the arm section 120 of the supporting arm apparatus 10, the control section 230 performs various kinds of operations in the whole body cooperative control and the ideal joint control. The function and configuration of the control section 230 will be described below in detail, but the whole body cooperative control and the ideal joint control have already been described in [2-2. Generalized inverse dynamics] and [2-3. Ideal joint control], and thus a description thereof will be omitted here.

The control section 230 includes a whole body cooperative control section 240 and an ideal joint control section 250.

The whole body cooperative control section 240 performs various kinds of operations related to the whole body cooperative control using the generalized inverse dynamics. In the present embodiment, the whole body cooperative control section 240 acquires a state (an arm state) of the arm section 120 on the basis of the state of the joint section 130 detected by the joint state detecting section 132. Further, the whole body cooperative control section 240 calculates a control value for the whole body cooperative control of the arm section 120 in the operation space on the basis of the arm state and the purpose of motion and the constraint condition of the arm section 120 using the generalized inverse dynamics. Note that the operation space refers to, for example, a space for describing a relation between force acting on the arm section 120 and acceleration generated in the arm section 120.

The whole body cooperative control section 240 includes an arm state acquiring section 241, an operation condition setting section 242, a virtual force calculating section 243, and an actual force calculating section 244.

The arm state acquiring section 241 acquires the state (the arm state) of the arm section 120 on the basis of the state of the joint section 130 detected by the joint state detecting section 132. Here, the arm state may mean the motion state of the arm section 120. For example, the arm state includes information such as a position, a speed, acceleration, or force of the arm section 120. As described above, the joint state detecting section 132 acquires information such as the rotational angle, the rotational angular velocity, the rotational angular acceleration, or the generated torque of each of the joint sections 130 as the state of the joint section 130. Further, as will be described later, the storage section 220 stores various kinds of information that is processed by the control apparatus 20, and in the present embodiment, the storage section 220 may store various kinds of information (arm information) related to the arm section 120, for example, the number of joint sections 130 and the number of links configuring the arm section 120, a connection state of the link and the joint section 130, and the length of the link. The arm state acquiring section 241 can acquire the corresponding information from the storage section 220. Thus, the arm state acquiring section 241 can acquire information such as the positions (coordinates) of the plurality of joint sections 130, a plurality of links, and the imaging section 140 on the space (that is, the shape of the arm section 120 or the position and posture of the imaging section 140) or force acting on each of the joint sections 130, the link, and the imaging section 140 on the basis of the state of the joint section 130 and the arm information. The arm state acquiring section 241 transmits the acquired arm information to the operation condition setting section 242.

The operation condition setting section 242 sets an operation condition in an operation related to the whole body cooperative control using the generalized inverse dynamics. Here, the operation condition may be the purpose of motion and the constraint condition. The purpose of motion may be various kinds of information related to a motion of the arm section 120. Specifically, the purpose of motion may be a target value of the position and posture (coordinates), a speed, acceleration, and force of the imaging section 140 or a target value of the position (coordinates), a speed, acceleration, and force of the plurality of joint sections 130 and a plurality of links of the arm section 120. The constraint condition may be various kinds of information for constricting the motion of the arm section 120. Specifically, the constraint condition may be coordinates of a region into which none of the components of the arm section should move, values of a speed and acceleration at which the arm section should not move, a value of force that should not be generated, or the like. Further, a constraint range of various kinds of physical quantities in the constraint condition may be set from ones that are difficult for the arm section 120 to implement structurally or may be appropriately set by the user. Further, the operation condition setting section 242 includes a physical model (for example, one in which the number of links configuring the arm section 120, the length of the link, the connection state of the link through the joint section 130, the movable region of the joint section 130, and the like are modelized) for the structure of the arm section 120, and may set the motion condition and the constraint condition by generating a control model in which a desired motion condition and a desired constraint condition are reflected in the physical model.

In the present embodiment, it is possible to appropriately set the purpose of motion and the constraint condition and cause the arm section 120 to perform a desired movement. For example, it is possible to set the target value of the position of the imaging section 140 as the purpose of motion and move the imaging section 140 to the target position, and it is also possible to set a movement constraint according to the constraint condition, for example, to prevent the arm section 120 from invading a certain region in a space and then drive the arm section 120.

As a specific example of the purpose of motion, for example, the purpose of motion may be a pivot movement serving as a turning movement in which the imaging section 140 moves within a plane of a cone having a medical procedure part as an apex, and an axis of the cone is used as a pivot axis in a state in which the photographing direction of the imaging section 140 is fixed to the medical procedure part. In the pivot movement, the turning movement may be performed in a state in which a distance between the imaging section 140 and a point corresponding to the apex of the cone is maintained constant. As the pivot movement is performed, it is possible to observe an observation part at an equal distance and at different angles, and thus it is possible to improve a convenience of the user performing surgery.

Further, for another specific example, the purpose of motion may be content controlling the generated torque in each of the joint sections 130. Specifically, the purpose of motion may be a power assist movement of controlling the state of the joint section 130 such that gravity acting on the arm section 120 is negated and controlling the state of the joint section 130 such that movement of the arm section 120 is supported in a direction of force given from the outside. More specifically, in the power assist movement, driving of each of the joint sections 130 is controlled such that each of the joint sections 130 generates the generated torque for negating external torque by gravity in each of the joint sections 130 of the arm section 120, and thus the position and posture of the arm section 120 are held in a certain state. When external torque is further applied from the outside (for example, from the user) in this state, driving of each of the joint sections 130 is controlled such that each of the joint sections 1 generates the generated torque in the same direction as the applied external torque. As the power assist movement is performed, when the user manually moves the arm section 120, the user can move the arm section 120 by small force, and thus a feeling of moving the arm section 120 in a non-gravity state can be given to the user. Further, it is possible to combine the pivot movement with the power assist movement.

Here, in the present embodiment, the purpose of motion may mean a movement (motion) of the arm section 120 implemented in the whole body cooperative control or may mean an instantaneous purpose of motion (that is, the target value in the purpose of motion) in the corresponding movement. For example, in the case of the pivot movement, performing the pivot movement by the imaging section 140 is the purpose of motion, but, for example, a value of the position or the speed of the imaging section 140 in the cone plane in the pivot movement is set as an instantaneous purpose of motion (the target value in the purpose of motion) while the pivot movement is being performed. Further, for example, in the case of the power assist movement, performing the power assist movement for supporting movement of the arm section 120 in the direction of force applied from the outside is the purpose of motion, but a value of the generated torque in the same direction as the external torque applied to each of the joint sections 130 is set as an instantaneous purpose of motion (the target value in the purpose of motion) while the power assist movement is being performed. In the present embodiment, the purpose of motion is a concept including both the instantaneous purpose of motion (for example, the target value of the position, the speed, or force of each component of the arm section 120 during a certain period of time) and movement of each component of the arm section 120 implemented over time as a result of continuously achieving the instantaneous purpose of motion. In each step in an operation for the whole body cooperative control in the whole body cooperative control section 240, the instantaneous purpose of motion is set each time, and the operation is repeatedly performed, so that a desired purpose of motion is finally achieved.

Note that, in the present embodiment, when the purpose of motion is set, the viscous drag coefficient in the rotary motion of each of the joint sections 130 may be appropriately set as well. As described above, the joint section 130 according to the present embodiment is configured to be able to appropriately adjust the viscous drag coefficient in the rotary motion of the actuator 430. Thus, as the viscous drag coefficient in the rotary motion of each of the joint sections 130 is also set at the time of setting of the purpose of motion, for example, it is possible to implement the state in which rotation is easily or not easily performed by force applied from the outside. For example, in the case of the power assist movement, as the viscous drag coefficient in the joint section 130 is set to be small, the user can move the arm section 120 by small force, and the user can have a non-gravity feeling. As described above, the viscous drag coefficient in the rotary motion of each of the joint sections 130 may be appropriately set according to content of the purpose of motion.

Note that a specific example of the purpose of motion will be described again in detail in [2-5. Specific example of purpose of motion].

Here, in the present embodiment, as will be described later, the storage section 220 may store a parameter related to the operation condition such as the purpose of motion or the constraint condition used in an operation related to the whole body cooperative control. The operation condition setting section 242 can set the constraint condition stored in the storage section 220 as the constraint condition used in the operation of the whole body cooperative control.

Further, in the present embodiment, the operation condition setting section 242 can set the purpose of motion by a plurality of methods. For example, the operation condition setting section 242 may set the purpose of motion on the basis of the arm state transmitted from the arm state acquiring section 241. As described above, the arm state includes information of the position of the arm section 120 and information of force acting on the arm section 120. Thus, for example, when the user manually moves the arm section 120, information related to how the user moves the arm section 120 is also acquired as the arm state through the arm state acquiring section 241. Thus, the operation condition setting section 242 can set, for example, the position to which the user has moved the arm section 120, a speed at which the user has moved the arm section 120, or force by which the user has moved the arm section 120 as the instantaneous purpose of motion on the basis of the acquired arm state. As the purpose of motion is set as described above, control is performed such that driving of the arm section 120 follows and supports movement of the arm section 120 by the user.

Further, for example, the operation condition setting section 242 may set the purpose of motion on the basis of an instruction input from the input section 210 by the user. As will be described later, the input section 210 is an input interface through which the user inputs, for example, information or a command related to driving control of the supporting arm apparatus 10 to the control apparatus 20, and in the present embodiment, the purpose of motion may be set on the basis of an operation input from the input section 210 by the user. Specifically, the input section 210 includes an operation means operated by the user such as a lever or a pedal, and, for example, the operation condition setting section 242 may set the position or the speed of each component of the arm section 120 as the instantaneous purpose of motion according to an operation of the lever, the pedal, or the like.

Further, for example, the operation condition setting section 242 may set the purpose of motion stored in the storage section 220 as the purpose of motion used in the operation of the whole body cooperative control. For example, in the case of the purpose of motion for causing the imaging section 140 to stop at a certain point in the space, coordinates of the certain point can be set as the purpose of motion in advance. Further, for example, in the case of the purpose of motion for causing the imaging section 140 to move along a certain trajectory in the space, coordinates of points indicating the certain trajectory can be set as the purpose of motion in advance. As described above, when the purpose of motion can be set in advance, the purpose of motion may be stored in the storage section 220 in advance. Further, for example, in the case of the pivot movement, the purpose of motion is limited to setting a position, a speed, or the like in the plane of the cone as the target value, and in the case of the power assist movement, the purpose of motion is limited to setting force as the target value. As described above, when the purpose of motion such as the pivot movement or the power assist movement is set in advance, for example, information related to a range or a type of the target value that can be set as the instantaneous purpose of motion in the purpose of motion may be stored in the storage section 220. The operation condition setting section 242 can include and set various kinds of information related to the purpose of motion as the purpose of motion.

Note that the user may appropriately set the method of setting the purpose of motion through the operation condition setting section 242, for example, according to the purpose of the supporting arm apparatus 10. Further, the operation condition setting section 242 may set the purpose of motion and the constraint condition by appropriately combining the above methods. Note that a priority of the purpose of motion may be set to the constraint condition stored in the storage section 220, and when there are a plurality of different purposes of motion, the operation condition setting section 242 may set the purpose of motion according to the priority of the constraint condition. The operation condition setting section 242 transmits the arm state, the set purpose of motion and the constraint condition to the virtual force calculating section 243.

The virtual force calculating section 243 calculates virtual force in the operation related to the whole body cooperative control using the generalized inverse dynamics. For example, a virtual force calculation process performed by the virtual force calculating section 243 may be a series of processes described above in (2-2-1. Virtual force calculating process). The virtual force calculating section 243 transmits the calculated virtual force $f_v$ to the actual force calculating section 244.

The actual force calculating section 244 calculates actual force in the operation related to the whole body cooperative control using the generalized inverse dynamics. For example, an actual force calculation process performed by the actual force calculating section 244 may be a series of processes described above in (2-2-2. Actual force calculating process). The actual force calculating section 244 transmits the calculated actual force (the generated torque) $\tau_a$ to the ideal joint control section 250. Further, in the present embodiment, the generated torque $\tau_a$ calculated by the actual force calculating section 244 is also referred to as a "control value" or a "control torque value" to mean a control value of the joint section 130 in the whole body cooperative control.

The ideal joint control section 250 performs various kinds of operations related to the ideal joint control using the generalized inverse dynamics. In the present embodiment, the ideal joint control section 250 corrects influence of a disturbance on the generated torque $\tau_a$ calculated by the actual force calculating section 244, and calculates the torque command value $\tau$ for implementing the ideal response of the arm section 120. The operation process performed by the ideal joint control section 250 corresponds to a series of processes described above in [2-3. Ideal joint control].

The ideal joint control section 250 includes a disturbance estimating section 251 and a command value calculating section 252.

The disturbance estimating section 251 calculates the disturbance estimation value $\tau_d$ on the basis of the torque command value $\tau$ and the rotational angular velocity calculated from the rotational angle q detected by the rotational angle detecting section 133. Here, the torque command value $\tau$ refers to the command value indicating the generated torque of the arm section 120 that is finally transmitted to the supporting arm apparatus 10. As described above, the disturbance estimating section 251 has a function corresponding to the disturbance observer 620 illustrated in FIG. 5.

The command value calculating section 252 calculates the torque command value $\tau$ serving as the command value indicating torque that is generated by the arm section 120 and finally transmitted to the supporting arm apparatus 10 using the disturbance estimation value $\tau_d$ calculated by the disturbance estimating section 251. Specifically, the command value calculating section 252 calculates the torque command value $\tau$ by adding the disturbance estimation value $\tau_d$ calculated by the disturbance estimating section 251 to $\tau^{ref}$ calculated from the ideal model of the joint section 130 expressed by Equation (12). For example, when the disturbance estimation value $\tau_d$ is not calculated, the torque command value $\tau$ is used as the torque target value $\tau^{ref}$. As described above, the function of the command value calculating section 252 corresponds to a function other than that of the disturbance observer 620 illustrated in FIG. 5.

As described above, in the ideal joint control section 250, a series of processes described above with reference to FIG. 5 is performed such that information is repeatedly exchanged between the disturbance estimating section 251 and the command value calculating section 252. The ideal joint control section 250 transmits the calculated torque command value $\tau$ to the drive control section 111 of the supporting arm apparatus 10. The drive control section 111 performs control of supplying an amount of electric current corresponding to the transmitted torque command value $\tau$ to the motor in the actuator of the joint section 130, controls the number of revolutions of the motor, and controls the rotational angle and the generated torque of the joint section 130.

In the supporting arm control system 1 according to the present embodiment, since driving control of the arm section 120 in the supporting arm apparatus 10 is continuously performed while a task using the arm section 120 is being performed, the above-described process is repeatedly performed in the supporting arm apparatus 10 and the control apparatus 20. In other words, the joint state detecting section 132 of the supporting arm apparatus 10 detects the state of the joint section 130, and transmits the detected state of the joint section 130 to the control apparatus 20. In the control apparatus 20, various kinds of operations related to the whole body cooperative control and the ideal joint control for controlling driving of the arm section 120 are performed on the basis of the state of the joint section 130, the purpose of motion, and the constraint condition, and the torque command value $\tau$ serving as the operation result is transmitted to the supporting arm apparatus 10. In the supporting arm apparatus 10, driving of the arm section 120 is controlled on the basis of the torque command value $\tau$, and the state of the joint section 130 during or after driving is detected by the joint state detecting section 132 again.

The description of the other components of the control apparatus 20 will now continue.

The input section 210 is an input interface through which the user inputs, for example, information or a command related to driving control of the supporting arm apparatus 10 to the control apparatus 20. In the present embodiment, on the basis of an operation input from the input section 210 by the user, driving of the arm section 120 of the supporting arm apparatus 10 may be controlled, and the position and posture of the imaging section 140 may be controlled. Specifically, as described above, as the user inputs instruction information related to an instruction of arm driving input from the input section 210 to the operation condition setting section 242, the operation condition setting section 242 may set the purpose of motion in the whole body cooperative control based on the instruction information. As described above, the whole body cooperative control is performed using the purpose of motion based on the instruction information input by the user, and thus driving of the arm section 120 according to the user's operation input is implemented.

Specifically, the input section 210 includes an operation means operated by the user such as a mouse, a keyboard, a touch panel, a button, a switch, a lever, and a pedal, for example. For example, when the input section 210 includes a pedal, the user can control driving of the arm section 120 by operating the pedal by foot. Thus, even when the user performs a treatment on the patient's medical procedure part using both hands, it is possible to adjust the position and posture of the imaging section 140, that is, the photographing position or the photographing angle of the medical procedure part through an operation of the pedal by foot.

The storage section 220 stores various kinds of pieces of information that are processed by the control apparatus 20. In the present embodiment, the storage section 220 can store various kinds of parameters used in the operation related to the whole body cooperative control and the ideal joint control performed by the control section 230. For example, the storage section 220 may store the purpose of motion and the constraint condition used in the operation related to the whole body cooperative control performed by the whole body cooperative control section 240. The purpose of motion stored in the storage section 220 may be a purpose of motion that can be set in advance so that the imaging section 140 can stop at a certain point in the space as described above, for example. Further, the constraint condition may be set by the user in advance according to the geometric configuration of the arm section 120, the purpose of the supporting arm apparatus 10, or the like and then stored in the storage section 220. Furthermore, the storage section 220 may store various kinds of information related to the arm section 120 used when the arm state acquiring section 241 acquires the arm state. Moreover, the storage section 220 may store, for example, the operation result in the operation related to the whole body cooperative control and the ideal joint control performed by the control section 230 and numerical values calculated in the operation process. As described above, the storage section 220 may store all parameters related to various kinds of processes performed by the control section 230, and the control section 230 can perform various kinds of processes while transmitting or receiving information to or from the storage section 220.

The function and configuration of the control apparatus 20 have been described above. The control apparatus 20 according to the present embodiment may be configured, for example, with various kinds of information processing apparatuses (arithmetic processing apparatuses) such as a personal computer (PC) or a server. Next, a function and configuration of the display apparatus 30 will be described.

The display apparatus 30 displays various kinds of information on the display screen in various formats such as text or an image, and visually notifies the user of the information. In the present embodiment, the display apparatus 30 displays an image captured by the imaging section 140 of the supporting arm apparatus 10 through the display screen. Specifically, the display apparatus 30 includes a function or component such as an image signal processing section (not illustrated) that performs various kinds of image processing on the image signal acquired by the imaging section 140 or a display control section (not illustrated) that performs control such that an image based on the processed image signal is displayed on the display screen. Further, the display apparatus 30 may have various kinds of functions and components that are equipped in a general display apparatus in addition to the above function or component. The display apparatus 30 corresponds to the display apparatus 550 illustrated in FIG. 1.

The functions and configurations of the supporting arm apparatus 10, the control apparatus 20, and the display apparatus 30 according to the present embodiment have been described above with reference to FIG. 6. Each of the above components may be configured using a versatile member or circuit, and may be configured by hardware specialized for the function of each component. Further, all the functions of the components may be performed by a CPU or the like. Thus, a configuration to be used may be appropriately changed according to a technology level when the present embodiment is carried out.

As described above, according to the present embodiment, the arm section 120 having the multi-link structure in the supporting arm apparatus 10 has at least 6 or more degrees of freedom, and driving of each of the plurality of joint sections 130 configuring the arm section 120 is controlled by the drive control section 111. Further, the medical apparatus is installed at the front edge of the arm section 120. As driving of each joint section 130 is controlled as described above, driving control of the arm section 120 having a high degree of freedom is implemented, and the supporting arm apparatus 10 for medical use having high operability for a user is implemented.

More specifically, according to the present embodiment, in the supporting arm apparatus 10, the state of the joint section 130 is detected by the joint state detecting section 132. Further, in the control apparatus 20, on the basis of the state of the joint section 130, the purpose of motion, and the constraint condition, various kinds of operations related to the whole body cooperative control using the generalized inverse dynamics for controlling driving of the arm section 120 are performed, and torque command value $\tau$ serving as the operation result are calculated. Furthermore, in the supporting arm apparatus 10, driving of the arm section 120 is controlled on the basis of the torque command value $\tau$. As described above, in the present embodiment, driving of the arm section 120 is controlled by the whole body cooperative control using the generalized inverse dynamics. Thus, driving control of the arm section 120 according to the force control is implemented, and the supporting arm apparatus having the high operability for the user is implemented. Further, in the present embodiment, in the whole body cooperative control, for example, control for implementing various kinds of purposes of motion for improving user convenience such as the pivot movement and the power assist movement can be performed. Furthermore, in the present embodiment, for example, various driving means for moving the arm section 120 manually or through an operation input from a pedal are implemented, and thus user convenience is further improved.

Further, in the present embodiment, the whole body cooperative control and the ideal joint control are applied to driving control of the arm section 120. In the ideal joint control, a disturbance component such as friction or inertia in the joint section 130 is estimated, and feedforward control is performed using the estimated disturbance component. Thus, even when there is a disturbance component such as friction, the ideal response can be implemented on driving of the joint section 130. Thus, small influence of vibration or the like, high-accuracy responsiveness, and high positioning accuracy or stability are implemented in driving control of the arm section 120.

Further, in the present embodiment, each of the plurality of joint sections 130 configuring the arm section 120 has a configuration suitable for the ideal joint control illustrated in FIG. 3, for example, and the rotational angle, the generated torque and the viscous drag coefficient of each of the joint sections 130 can be controlled according to an electric current value. As described above, driving of each of the joint sections 130 is controlled according to an electric current value, and driving of each of the joint sections 130 is controlled according to the whole body cooperative control while detecting the entire state of the arm section 120, and thus the counter balance is unnecessary, and the small supporting arm apparatus 10 is implemented.

2-5. Regarding Sensor Value Estimation and Trouble Determination

In the above-described configuration, the whole body cooperative control section 240 is notified of the angle, the angular velocity, and the torque observed by the actuator 430. The whole body cooperative control section 240 calculates generated torque of the joint sections 513$a$ to 513$c$ necessary for the arm section 512 to perform a desired operation. At this time, the observed angle, angular velocity and torque value, and physical information (number of joints, link length, inertia, and inertia moment) held inside are used. Each actuator 430 is notified of the calculated generated torque, and control is performed such that the actuator 430 generates the torque.

The above-described configuration is a support arm system (for medical use) including the plurality of actuators (VA) 430. Here, the actuators (VA) 430 have the following features.

(a) A sensor (such as the encoder 427) is installed for detecting a displacement of an output stage.
(b) A sensor (such as the torque sensor 428) is installed for detecting force acting on the output stage.
(c) An output torque value is received from the controller, and this is used as a control target value to perform an operation.
(d) A controller is notified of the values detected by the sensors of (a) and (b) above as control observation values.

In addition, the controller here includes control apparatuses of the actuators (VA) 430 having the following features.
(a) Physical information of the supporting arm is held inside.
(b) All the actuators (VA) 430 are notified of the output torque values on the basis of the information whose notifications are issued by the actuators (VA) 430.

In the present embodiment, the immediately following joint angles (angular velocity and angular acceleration) of the actuators (VA) 430 are predicted on the basis of the generated torque $\tau_a$ (torque command value), the torque values observed by the actuators (VA) 430, the immediately previous angle, and the observation value of angular velocity, and the sensor value of the encoder 427 is estimated (predicted). In addition, the sensor value of the torque sensor 428 in the previous cycle is predicted on the basis of the generated torque $\tau_a$ (torque command value) in the previous cycle, the encoder value (angular velocity) in the previous cycle which is observed by the encoder 427, and the encoder value (angular acceleration) in the current cycle which is observed by the encoder 427. Then, the predicted values are compared with the detection values (sensor values) of the encoder 427 and the torque sensor 428 to perform trouble detection on the encoder 427 and the torque sensor 428.

This makes it possible to predict, from one sensor value of the actuator 430, another sensor value of the same actuator 430 for each of the plurality of actuators 430 installed in the supporting arm even in the state in which unexpected external force is applied to the supporting arm.

Specifically, the use of the predicted values allows sensor trouble to be sensed as follows.
(A) From the torque sensor value of the actuator 430, the angle sensor value of the same actuator 430 is estimated, and trouble/malfunction is sensed depending on whether it agrees with the actually measured data.
(B) From the angle sensor value of the actuator 430, the torque sensor value of the same actuator 430 is estimated, and trouble/malfunction is sensed depending on whether it agrees with the actually measured data.

Figure 7:
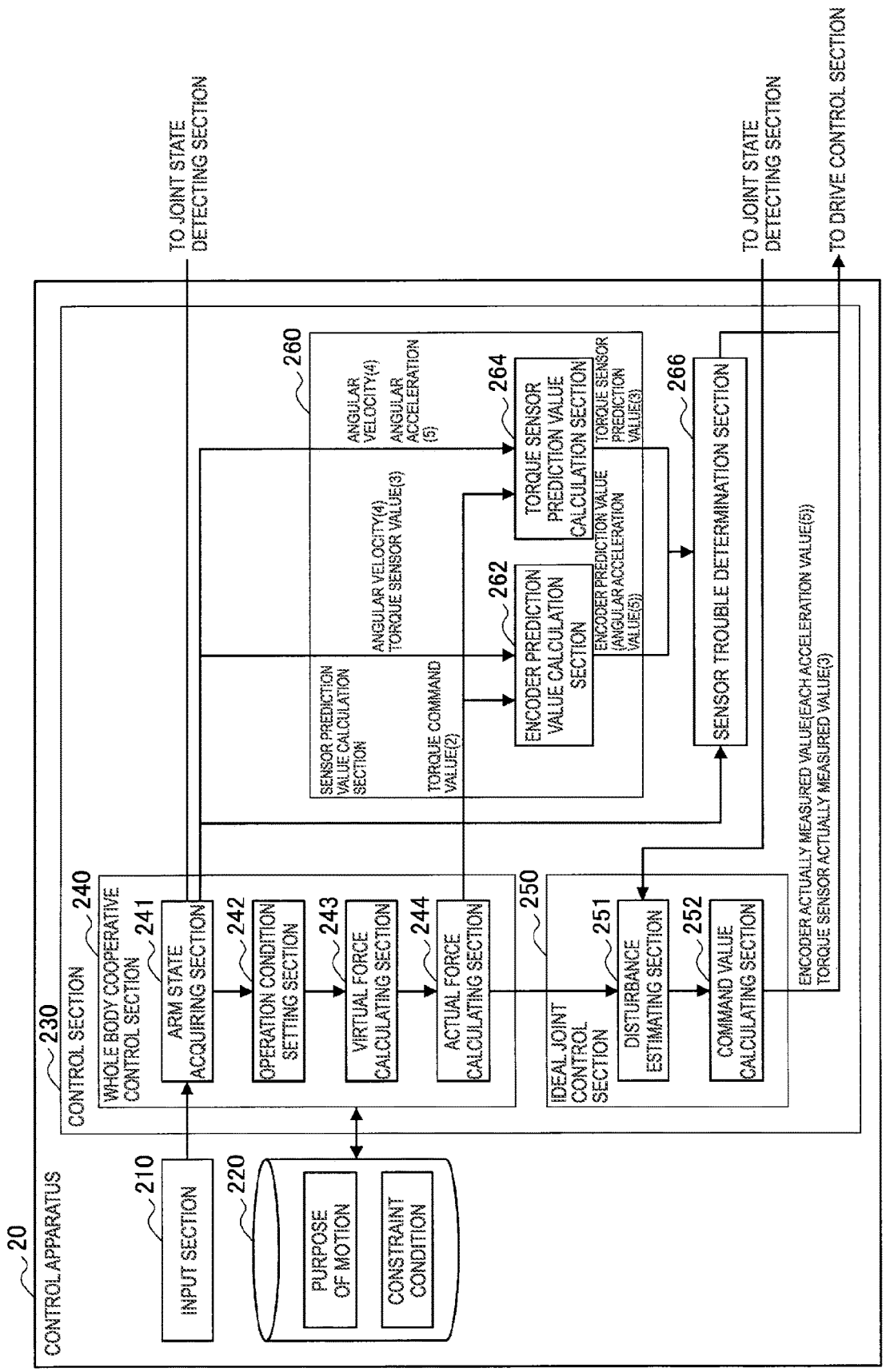
FIG. 7 is a schematic diagram illustrating a component for sensor value estimation and trouble determination.

FIG. 7 is a schematic diagram illustrating components for sensor value estimation and trouble determination. In the control section 230 illustrated in FIG. 6, a sensor prediction value calculation section 260 and a sensor trouble determination section 266 are added. The sensor prediction value calculation section 260 includes an encoder prediction value calculation section 262 and a torque sensor prediction value calculation section 264. The encoder prediction value calculation section 262 predicts a sensor value of the encoder 427, and outputs an encoder prediction value. The torque sensor prediction value calculation section 264 predicts a sensor value of the torque sensor 428, and outputs a torque prediction value.

The sensor trouble determination section 266 compares the encoder prediction value with a detection value (actually measured value) of the encoder 427 to perform trouble determination on the encoder 427. In addition, the sensor trouble determination section 266 compares the torque prediction value with a detection value (actually measured value) of the torque sensor 428 to perform trouble determination on the torque sensor 428. In any case, in the case where there is a great discrepancy between the prediction value and the detection value (actually measured value), trouble determination is performed.

Figure 8:
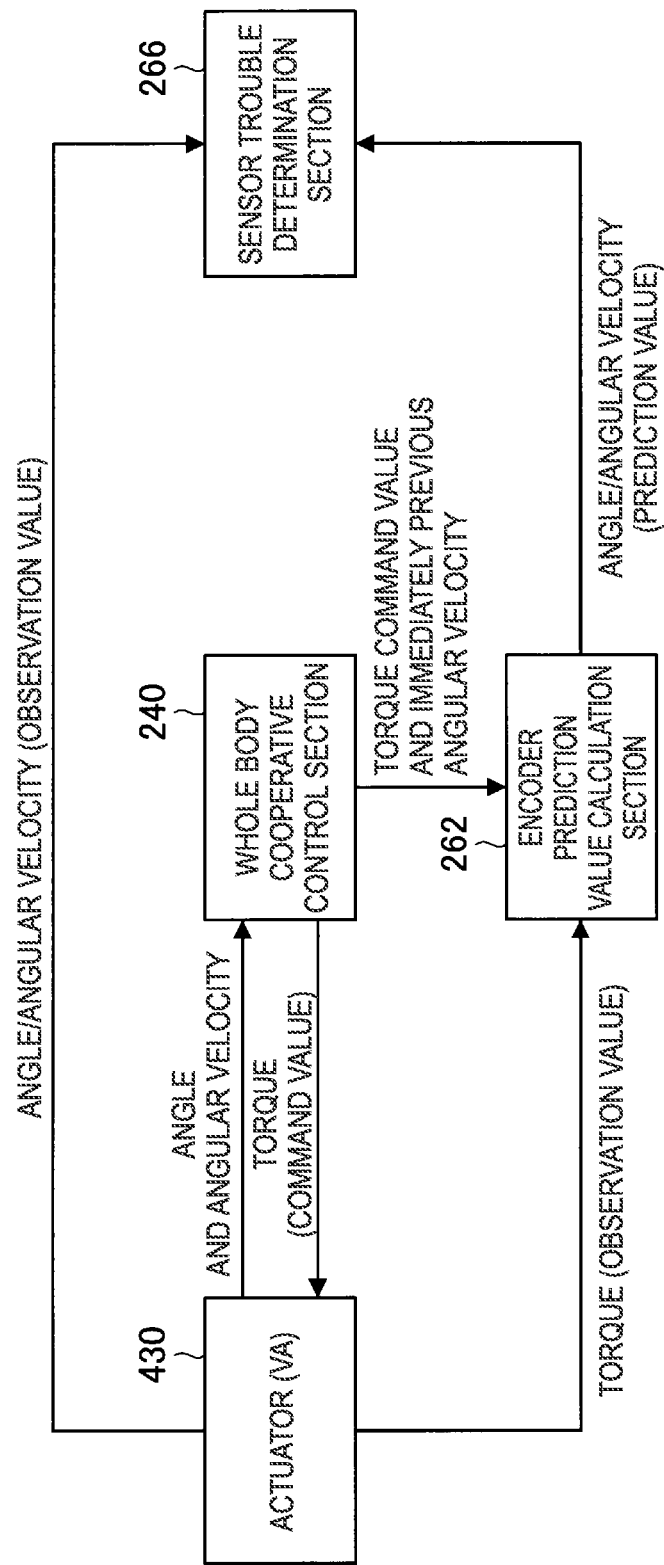
FIG. 8 is a schematic diagram illustrating an encoder prediction value calculation section and a peripheral component thereof.

FIG. 8 is a schematic diagram illustrating the encoder prediction value calculation section 262 and a peripheral component thereof. The angle and angular velocity detected by the encoder 427 are sent to the whole body cooperative control section 240 from the actuator 430 of the joint section 130. The torque command value $\tau_a$ calculated by the whole body cooperative control section 240 is sent to the actuator 430. Note that FIG. 8 does not illustrate the ideal joint control section 250.

In the case where trouble detection is performed on the encoder 427, the torque value observed by the actuator and the generated torque $\tau_a$ calculated by the whole body cooperative control section 240 are conveyed to the encoder prediction value calculation section 262 in addition to a basic control loop to predict the angle and the angular velocity. The angle and angular velocity (angle and angular velocity observation value) observed by the actuator 430 and the predicted angle and angular velocity are sent to the sensor trouble determination section 266. The sensor trouble determination section 266 compares the observation value with the prediction value, and determines sensor trouble in the case where there is a different greater than or equal to a threshold set in advance. Note that the prediction values of an angle, angular velocity, and angular acceleration can be converted to and from each other on the basis of a control cycle, and thus any of the values may be used for trouble determination.

Specifically, the encoder prediction value calculation section 262 uses the following equation of angular motion to calculate and predict the behavior of each joint.

[Math. 12]

$$I\ddot{q} = \tau_a + \tau_e - \mu\dot{q} \quad (13)$$

where
$\tau_a$: torque (torque command value which will be represented as (2) below) generated by the actuator (VA)
$\tau_e$: torque (which will be represented as (3) below) generated by external force such as gravity
$\dot{q}$: angular velocity (which will be represented as (4) below) of the actuator (VA)
$\ddot{q}$: angular acceleration (which will be represented as (5) below) of the actuator (VA)
$I$: inertia moment (which will be represented as (6) below) around the shaft of the arm
$\mu$: viscous drag (which will be represented as (7) below) around the shaft Note that the equation of motion expressed as Equation (13) is basically similar to Equation (12), but the value of inertia moment is different. In Equation (13), inertia moment $I$ is the inertia moment of the arm section 512 in each joint section. The following uses Equation (13) and the respective values (2) to (7) to predict a sensor value as follows.

Figure 9:
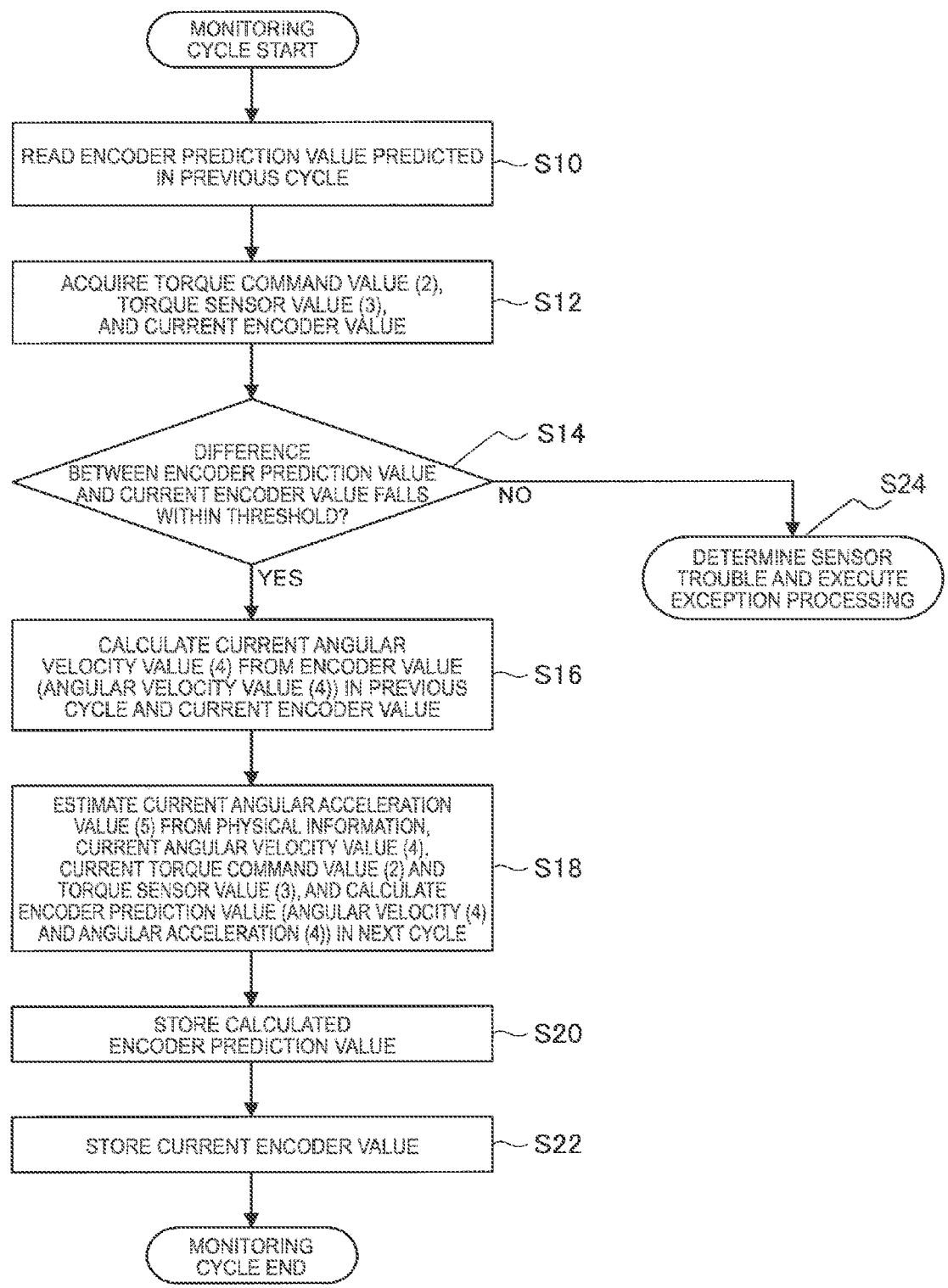
FIG. 9 is a flowchart illustrating processing of estimating an encoder value from a torque sensor value for trouble determination.

An encoder value is estimated by obtaining the immediately following left side value from the three terms on the right side of Equation (13). FIG. 9 is a flowchart illustrating processing of estimating an encoder value from a torque sensor value for trouble determination. First, in step S10, the encoder prediction value (angular velocity (4)) predicted in the previous cycle is read. In next step S12, the torque command value (2), the torque sensor value (3), and the current encoder value (sensor value) are acquired.

In next step S14, it is determined whether or not the difference between the encoder prediction value read in step S10 and the current encoder value acquired in step S12 falls within a predetermined threshold. In the case where the difference falls within the threshold, the flow proceeds to step S16. In step S16, the current angular velocity value (4) is calculated on the basis of the encoder value (angular velocity value (4)) in the previous cycle and the current encoder value (angular velocity value (4)). In the case where the flow proceeds to step S16, it is possible to determine that the encoder is in order. Accordingly, it is possible to set the encoder value in the previous cycle or the current encoder value as the current angular velocity value (4).

In next step S18, the current angular acceleration (5) is estimated on the basis of Equation (13) from the physical information (inertia moment (6) and viscous drag (7)), the current angular velocity value (4) obtained in step S16, and the current torque command value (2) and torque sensor value (3) acquired in step S12. Specifically, the current torque command value (2), the torque sensor value (3), and the current angular velocity value (4) are respectively substituted into the first term, the second term, and the third term on the right side of Equation (13) to calculate the angular acceleration (5) on the left side. Then, the angular velocity (4) is calculated from the angular acceleration (5). Note that the angular velocity (4) can be obtained by integrating the angular acceleration (5) on the basis of the control cycle. The angular velocity (4) calculated here is used as the encoder prediction value (angular velocity (4)) in step S10 of the next cycle. In next step S20, the encoder prediction value calculated in step S18 is stored. In next step S22, the current encoder value (angular velocity (4)) is stored. The encoder value stored in step S22 is used to calculate the angular velocity (4) in step S16 of the next cycle. This terminates the monitoring cycle.

In addition, in the case where the difference exceeds the predetermined threshold in step S14, the flow proceeds to step S24. In step S24, it is determined that the sensor (encoder) has trouble, and exception processing is executed.

Figure 10:
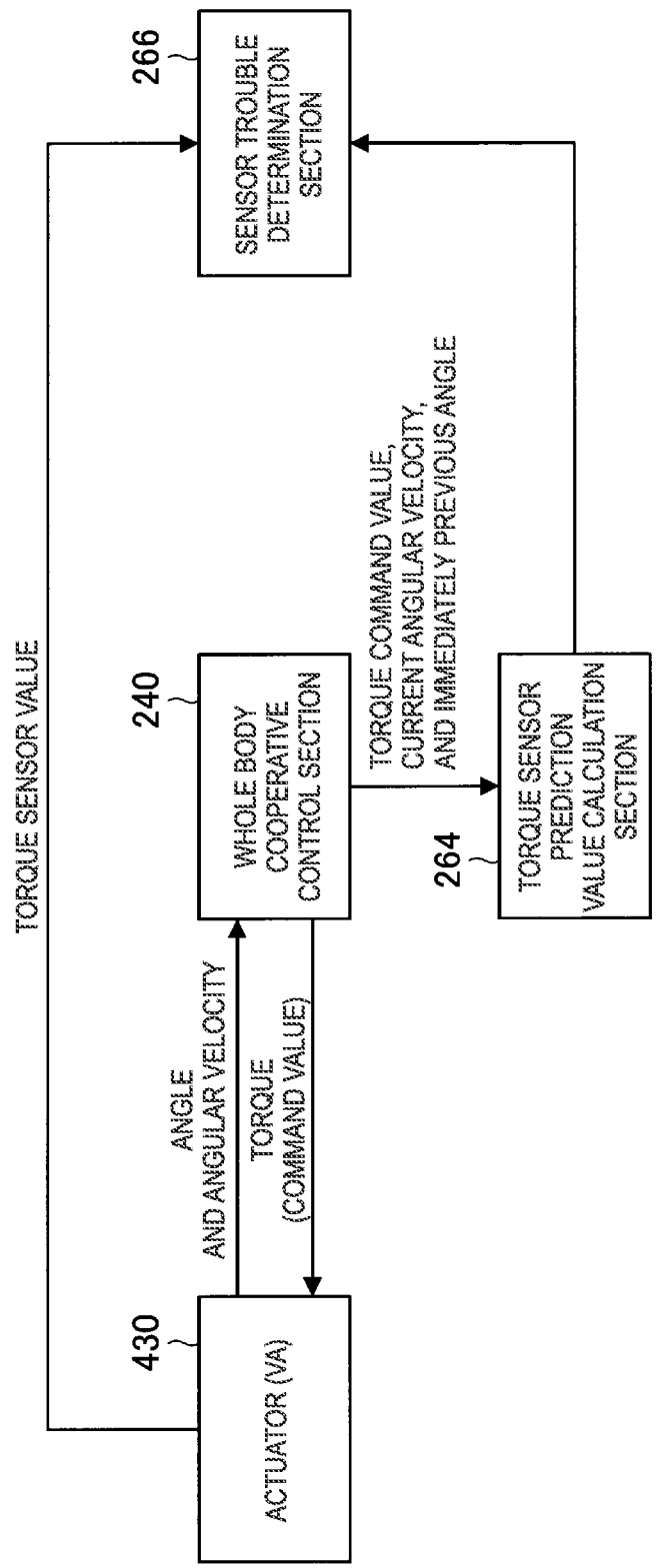
FIG. 10 is a schematic diagram illustrating a torque sensor estimation value calculation section and a peripheral component thereof.

FIG. 10 is a schematic diagram illustrating the torque sensor prediction value calculation section 264 and a peripheral component thereof. Similarly to FIG. 8, the angle and angular velocity detected by the encoder 427 are sent to the whole body cooperative control section 240 from the actuator 430 of the joint section 130. The torque command value $\tau_a$ calculated by the whole body cooperative control section 240 is sent to the actuator 430. FIG. 10 does not also illustrate the ideal joint control section 250.

In the case where trouble detection is performed on the torque sensor 428, the torque value observed by the actuator 430 and the generated torque $\tau_a$ calculated by the whole body cooperative control section 240 are conveyed to the torque sensor prediction value calculation section 264 in addition to a basic control loop to predict the torque. The torque observed by the actuator 430 and the torque prediction value are sent to the sensor trouble determination section 266. The sensor trouble determination section 266 compares the observation value with the prediction value, and determines sensor trouble in the case where there is a different greater than or equal to a threshold set in advance.

Figure 11:
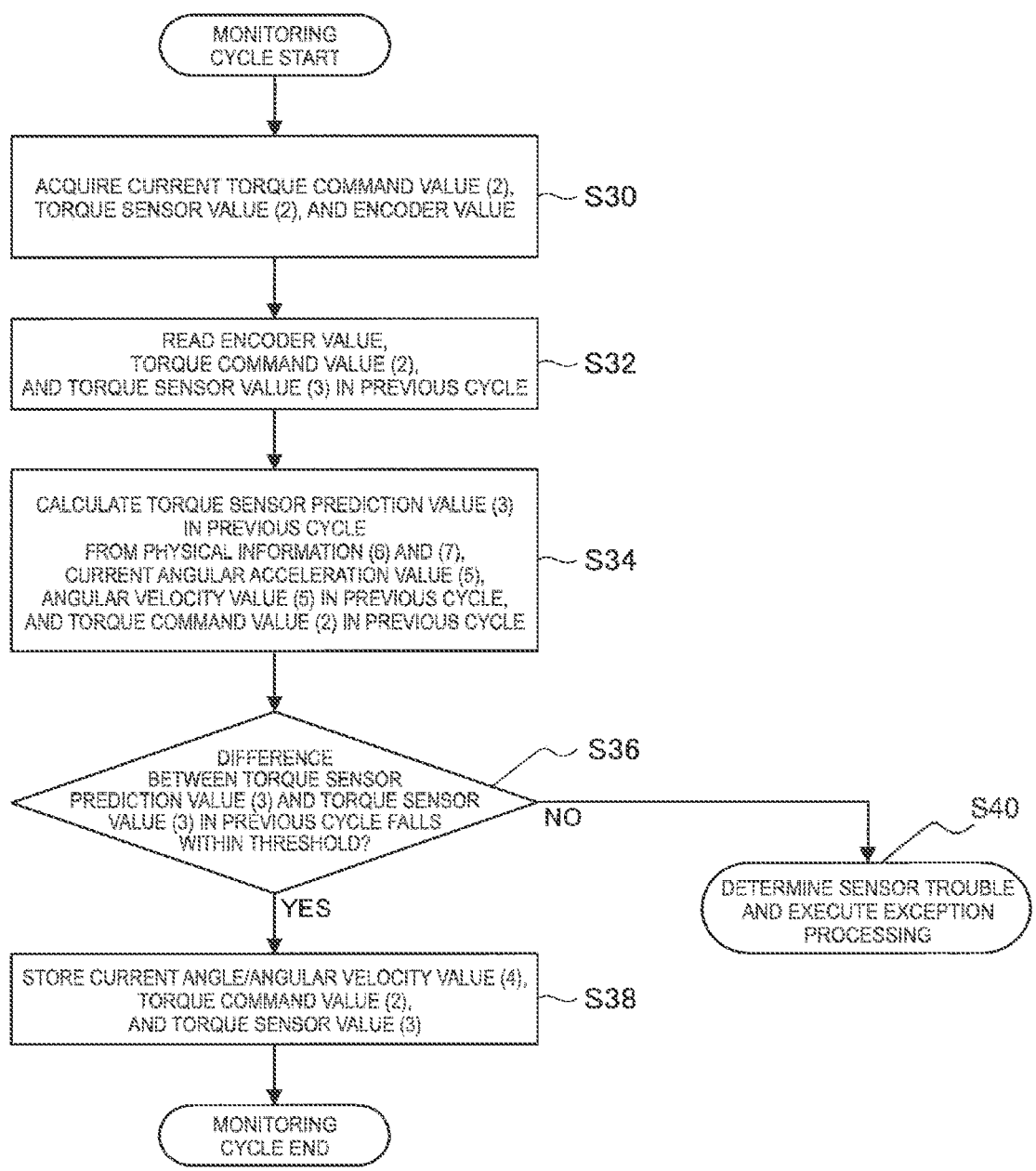
FIG. 11 is a flowchart illustrating processing of estimating a torque sensor value for trouble determination.

The torque sensor value is estimated by obtaining the second term on the right side of Equation (13) from the first term on the left side and the first and third terms on the right side. FIG. 11 is a flowchart illustrating processing of estimating a torque sensor value for trouble determination. First, in step S30, the current torque command value (2), torque sensor value (3), and encoder value (angular acceleration (5)) are acquired. In next step S32, the encoder value (angular velocity (4)), torque command value (2), and torque sensor value (3) in the previous cycle are read. In next step S34, the torque sensor prediction value (3) in the previous cycle is calculated on the basis of Equation (13) from the physical information (inertia moment (6) and viscous drag (7)), the encoder value (current angular acceleration (5)) acquired in step S30, and the angular velocity (4) in the previous cycle and the torque command value (2) in the previous cycle which are read in step S32. Specifically, the torque command value (2) in the previous cycle, the angular velocity (4) in the previous cycle, and the current angular acceleration (5) are respectively substituted into the first term on the right side, the third term on the right side, and the left side of Equation (13) to calculate the torque sensor prediction value (3) in the previous cycle in the second term on the right side.

In next step S36, it is determined whether or not the difference between the torque sensor prediction value (3) in the previous cycle which is calculated in step S34 and the torque sensor value (3) in the previous cycle which is read in step S32 falls within a predetermined threshold. In the case where the difference falls within the predetermined threshold, the flow proceeds to step S38. In the case where the flow proceeds to step S38, the difference falls within the predetermined threshold, so that it can be determined that the torque sensor 428 is in order.

In step S38, the current angle and angular velocity value (4), torque command value (2), and torque sensor value (3) are stored. The current angular velocity value (4), torque command value (2), and torque sensor value (3) stored here are respectively read in step S32 of the next control cycle as the encoder value, the torque command value (2), and the torque sensor value (3) in the previous cycle. This terminates the monitoring cycle.

In addition, in the case where the difference exceeds the predetermined threshold in step S36, the flow proceeds to step S40. In step S40, it is determined that the torque sensor 428 has trouble, and exception processing is executed.

As described above, in the case where a torque sensor value is predicted, estimation is performed from the encoder value (angular acceleration (5)) caused by generated torque. Accordingly, the torque sensor value (3) in the immediately previous cycle is estimated. More specifically, torque is generated, and then acceleration is generated in an actuator 480, and an encoder value is detected. In the case where a torque sensor value is estimated, prediction is performed in the inverse path, so that, in Equation (13), the external force torque (3) in the previous cycle is predicted on the basis of the angular acceleration (5) in the current cycle, the torque command value (2) in the previous cycle, and the angular velocity (4) in the previous cycle, and the torque sensor value in the previous cycle is compared with the prediction value in the previous cycle for trouble determination.

As described above, the sensor trouble determination section 266 can determine whether or not the encoder 427 and the torque sensor 428 have trouble. When the trouble of any of the sensors is determined, it is possible to use one of the actually measured values to calculate the other prediction value. Accordingly, there is no need to provide a new sensor for trouble determination. Thus, the actuator 430 is not made larger for trouble determination, so that it is possible to miniaturize the actuator 430. Note that trouble determination may be performed on only one of the encoder 427 and the torque sensor 428, or on both of them in parallel.

3. Application Example

The technology according to the present disclosure is applicable to a variety of products. For example, the technology according to the present disclosure may be applied to an endoscopic surgical system.

Figure 13:
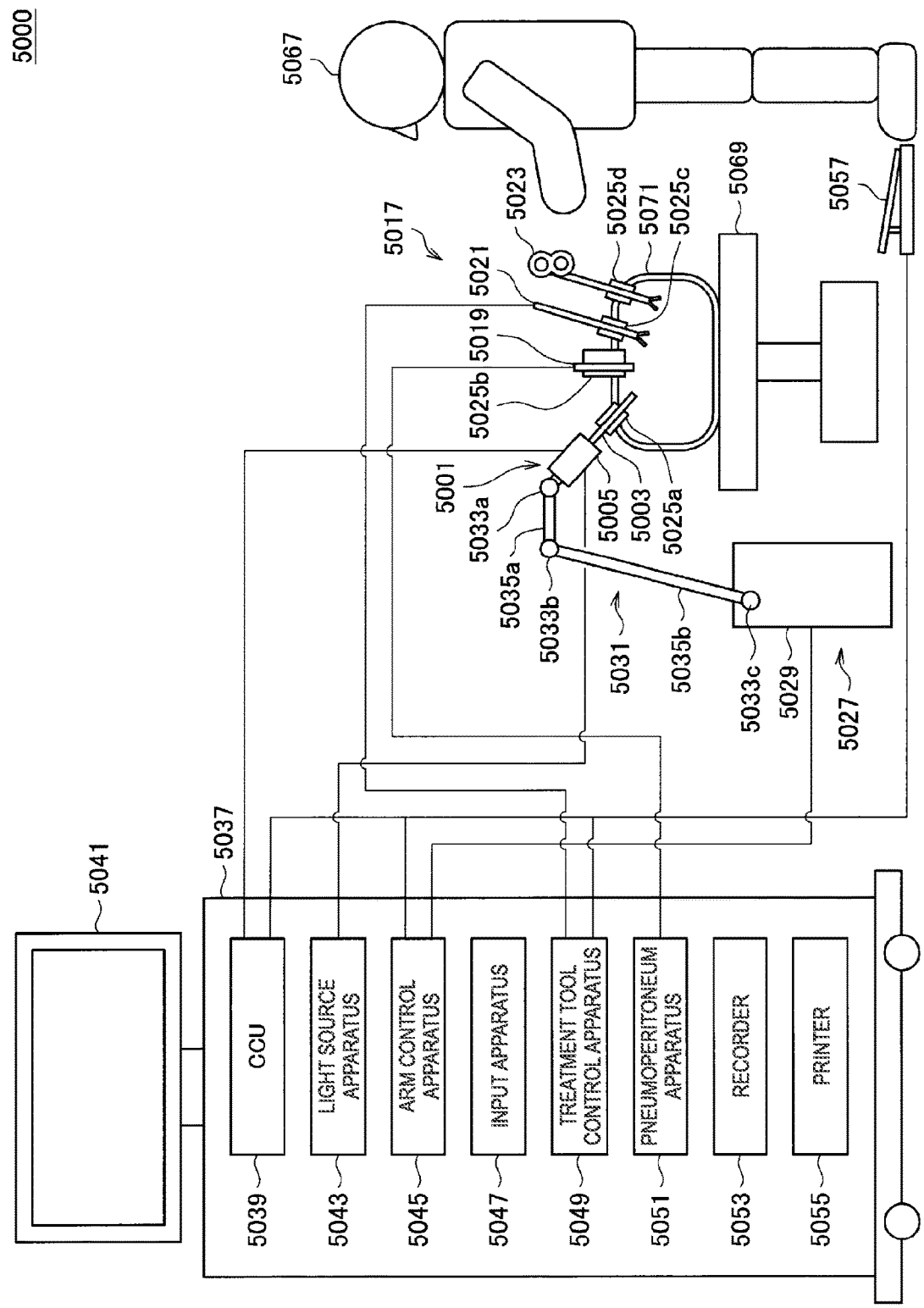
FIG. 13 is a diagram illustrating an example of a schematic configuration of an endoscopic surgical system 5000 to which technology according to the present disclosure can be applied.

FIG. 13 is a diagram illustrating an example of the schematic configuration of an endoscopic surgical system 5000 to which the technology according to the present disclosure can be applied. FIG. 13 illustrates a state in which a surgeon (doctor) 5067 performs surgery on a patient 5071 on a patient bed 5069 using the endoscopic surgical system 5000. As illustrated in FIG. 13, the endoscopic surgical system 5000 includes an endoscope 5001, other surgical instruments 5017, a supporting arm apparatus 5027 that supports the endoscope 5001, and a cart 5037 on which various apparatuses for endoscopic surgery are provided.

In endoscopic surgery, instead of opening up the abdomen by cutting the abdominal wall, tubular hole-opening tools called trocars 5025a to 5025d are used to puncture the abdominal wall in a plurality of places. Subsequently, the lens tube 5003 of the endoscope 5001 and the other surgical instruments 5017 are inserted into the body cavity of the patient 5071 from the trocars 5025a to 5025d. In the illustrated example, a pneumoperitoneum tube 5019, an energy treatment tool 5021, and forceps 5023 are inserted into the body cavity of the patient 5071 as the other surgical instruments 5017. In addition, the energy treatment tool 5021 is a treatment tool that makes incisions into and ablates tissues, or seals blood vessels or the like, with a high-frequency electric current or ultrasonic vibration. However, the surgical instruments 5017 illustrated in the diagram are merely an example, and any of various types of surgical instruments, for example, tweezers, retractors, and the like which are typically used in endoscopic surgery may also be used as the surgical instruments 5017.

An image of the surgical site inside the body cavity of the patient 5071 captured by the endoscope 5001 is displayed on a display apparatus 5041. The surgeon 5067 uses the energy treatment tool 5021 and the forceps 5023 to perform treatments, such as excising an affected area, for example, while viewing in real-time the image of the surgical site displayed on the display apparatus 5041. Note that, although omitted from the diagram, the pneumoperitoneum tube 5019, the energy treatment tool 5021, and the forceps 5023 are supported by a person such as the surgeon 5067 or an assistant during surgery.

(Supporting Arm Apparatus)

The supporting arm apparatus 5027 is provided with an arm section 5031 that extends from a base section 5029. In the illustrated example, the arm section 5031 includes joint sections 5033a, 5033b, and 5033c, as well as links 5035a and 5035b, and is driven in accordance with the control from the arm control apparatus 5045. The endoscope 5001 is supported by the arm section 5031, and the position and attitude thereof are hereby controlled. With this arrangement, locking of the endoscope 5001 at a stable position may be realized.

(Endoscope)

The endoscope 5001 includes the lens tube 5003 having a region of certain length from the front end that is inserted into the body cavity of the patient 5071, and a camera head 5005 connected to the base end of the lens tube 5003. In the illustrated example, the endoscope 5001 configured as a so-called rigid scope including the rigid lens tube 5003 is illustrated, but the endoscope 5001 may also be configured as a so-called flexible scope including the flexible lens tube 5003.

On the front end of the lens tube 5003, there is provided an opening into which an objective lens is fitted. A light source apparatus 5043 is connected to the endoscope 5001. Light generated by the light source apparatus 5043 is guided up to the front end of the lens tube by a light guide extending inside the lens tube 5003, and is radiated through the objective lens towards an observation target inside the body cavity of the patient 5071. Note that the endoscope 5001 may be a forward-viewing scope, an oblique-viewing scope, or a side-viewing scope.

An optical system and an image sensor are provided inside the camera head 5005, and reflected light (observation light) from the observation target is condensed onto the image sensor by the optical system. Observation light is photoelectrically converted by the image sensor, and the electrical signal corresponding to the observation light, or in other words, the image signal corresponding to the observed image, is generated. The image signal is transmitted as RAW data to a camera control unit (CCU) 5039. Note that the camera head 5005 is provided with a function of adjusting the magnification and the focus distance by appropriately driving the optical system.

Note that, to support stereoscopic vision (3D display) or the like, for example, the camera head 5005 may also be provided with a plurality of image sensors. In this case, a plurality of relay optical subsystems are provided inside the lens tube 5003 to guide the observation light to each of the plurality of image sensors.

(Various Apparatuses Mounted on Cart)

The CCU 5039 includes a central processing unit (CPU), a graphics processing unit (GPU), and the like, and centrally controls the operations of the endoscope 5001 and the display apparatus 5041. Specifically, the CCU 5039 subjects an image signal received from the camera head 5005 to various types of image processing for displaying an image based on the image signal, such as development processing (demosaic processing), for example. The CCU 5039 provides an image signal that has been subjected to such image processing to the display apparatus 5041. In addition, the CCU 5039 transmits a control signal to the camera head 5005 to control the driving thereof. The control signal can include information related to an imaging condition, such as the magnification and focus distance.

The display apparatus 5041, in accordance with the control from the CCU 5039, displays an image based on an image signal subjected to image processing by the CCU 5039. In the case where the endoscope 5001 supports imaging at high resolution such as 4K (3840 horizontal pixels×2160 vertical pixels) or 8K (7680 horizontal pixels×4320 vertical pixels), and/or supports 3D display, for example, an apparatus compatible with each of them and capable of high-resolution display and/or capable of 3D display can be used as the display apparatus 5041. In the case where imaging at high resolution such as 4K or 8K is supported, an apparatus with a size of 55 inches or more can be used as the display apparatus 5041 to thereby obtain an even deeper sense of immersion. Also, depending on the application, a plurality of display apparatuses 5041 different in resolution and size may also be provided.

The light source apparatus 5043 includes a light source such as a light emitting diode (LED), for example, and supplies the endoscope 5001 with irradiating light when imaging the surgical site.

The arm control apparatus 5045 includes a processor such as a CPU, for example, and by operating in accordance with a predetermined program, controls the driving of the arm section 5031 of the supporting arm apparatus 5027 in accordance with a predetermined control scheme.

An input apparatus 5047 is an input interface with respect to the endoscopic surgical system 5000. Through the input apparatus 5047, the user is able to input various kinds of information and instructions into the endoscopic surgical system 5000. For example, through the input apparatus 5047, the user inputs various kinds of information related to surgery, such as physical information about the patient, and information about surgical procedures. In addition, for example, through the input apparatus 5047, the user inputs instructions to drive the arm section 5031, instructions to change the imaging conditions of imaging by the endoscope 5001 (such as the type of irradiating light, the magnification, and the focus distance), instructions to drive the energy treatment tool 5021, and the like.

The type of the input apparatus 5047 is not limited, but the input apparatus 5047 may be any of various publicly-known types of input apparatuses. For example, apparatuses such as a mouse, a keyboard, a touch panel, a switch, a footswitch 5057, and/or a lever may be applied as the input apparatus 5047. In the case where a touch panel is used as the input apparatus 5047, the touch panel may be provided on the display screen of the display apparatus 5041.

Alternatively, the input apparatus 5047 is a device worn by the user, such as an eyeglasses-style wearable device or a head-mounted display (HMD), for example, and various inputs are performed in accordance with the user's gestures or gaze detected by these devices. Also, the input apparatus 5047 includes a camera capable of detecting the user's movement, and various inputs are performed in accordance with the user's gestures or gaze detected from a video captured by the camera. Furthermore, the input apparatus 5047 includes a microphone capable of picking up the user's voice, and various inputs are performed by voice via the microphone. In this way, by configuring the input apparatus 5047 to be capable of receiving the inputs of various types of information in a non-contact manner, a user belonging to a clean area in particular (for example, the surgeon 5067) becomes able to operate an apparatus belonging to an unclean area in a non-contact manner. In addition, since the user becomes able to operate an apparatus without taking his or her hands away from the tools the user is holding, user convenience is improved.

The treatment tool control apparatus 5049 controls the driving of the energy treatment tool 5021 to cauterize or make incisions into tissue, seal blood vessels, or the like. The pneumoperitoneum apparatus 5051 delivers gas into the body cavity of the patient 5071 through the pneumoperitoneum tube 5019 to inflate the body cavity for the purpose of securing a field of view for the endoscope 5001 and securing a workspace for the surgeon. The recorder 5053 is an apparatus capable of recording various types of information related to surgery. The printer 5055 is an apparatus capable of printing out various types of information related to surgery in various formats, such as text, images, or graphs.

A particularly characteristic configuration in the endoscopic surgical system 5000 will be described below in more detail.

(Supporting Arm Apparatus)

The supporting arm apparatus 5027 includes a base section 5029 which acts as a base, and an arm section 5031 which extends from the base section 5029. In the illustrated example, the arm section 5031 includes a plurality of joint sections 5033a, 5033b, and 5033c, as well as a plurality of links 5035a and 5035b coupled by the joint section 5033b, but in FIG. 13, for the sake of simplicity, the configuration of the arm section 5031 is illustrated in a simplified manner. In actuality, factors such as the shapes, numbers, and arrangement of the joint sections 5033a to 5033c and the links 5035a and 5035b, and the directions of the rotation axes of the joint sections 5033a to 5033c can be set appropriately such that the arm section 5031 has the desired degrees of freedom. For example, the arm section 5031 preferably can be configured to have six or more degrees of freedom. With this arrangement, it is possible to move the endoscope 5001 freely within the movable range of the arm section 5031, and thus it is possible to insert the lens tube 5003 of the endoscope 5001 into the body cavity of the patient 5071 from a desired direction.

The joint sections 5033a to 5033c include an actuator, and the joint sections 5033a to 5033c are configured to be rotatable about a predetermined rotation axis in accordance with the driving of the actuator. By controlling the driving of the actuator with the arm control apparatus 5045, the rotational angle of each of the joint sections 5033a to 5033c is controlled, and the driving of the arm section 5031 is controlled. With this arrangement, control of the position and the attitude of the endoscope 5001 may be realized. At this time, the arm control apparatus 5045 is capable of controlling the driving of the arm section 5031 with any of various publicly-known types of control methods, such as force control or position control.

For example, by having the surgeon 5067 perform appropriate an operation input via the input apparatus 5047 (including the footswitch 5057), the driving of the arm section 5031 may be controlled appropriately by the arm control apparatus 5045 in accordance with the operation input, and the position and the attitude of the endoscope 5001 may be controlled. By such control, after moving the endoscope 5001 on the front end of the arm section 5031 from a given position to a given position, the endoscope 5001 can be supported fixedly at the new position. Note that the arm section 5031 may also be operated by what is called a master-slave method. In this case, the arm section 5031 may be operated remotely by a user via the input apparatus 5047 installed in a location distant from the operating room.

In addition, in the case where force control is applied, the arm control apparatus 5045 may receive external force from the user, and drive the actuator of each of the joint sections 5033a to 5033c such that the arm section 5031 moves smoothly in response to the external force, also known as power assist control. With this arrangement, when the user moves the arm section 5031 while touching the arm section 5031 directly, the arm section 5031 can be moved with comparatively light force. Consequently, it is possible to move the endoscope 5001 more intuitively with a simpler operation, and user convenience can be improved.

Herein, in endoscopic surgery, typically the endoscope 5001 has been supported by a doctor called a scopist. In contrast, by using the supporting arm apparatus 5027, it is possible to keep the position of the endoscope 5001 fixed more reliably without manual work, and thus an image of the surgical site can be obtained consistently, making it possible to perform surgery smoothly.

Note that the arm control apparatus 5045 does not necessarily have to be provided on the cart 5037. In addition, the arm control apparatus 5045 does not necessarily have to be one apparatus. For example, the arm control apparatus 5045 may also be provided in each of the joint sections 5033a to 5033c of the arm section 5031 of the supporting arm apparatus 5027, and the plurality of arm control apparatuses 5045 may cooperate with each other to realize driving control of the arm section 5031.

(Light Source Apparatus)

The light source apparatus 5043 supplies the endoscope 5001 with irradiating light when imaging the surgical site. The light source apparatus 5043 includes a white light source including an LED, a laser light source, or a combination thereof, for example. At this time, in the case where the white light source includes a combination of RGB laser light sources, the output intensity and output timing of each color (each wavelength) can be controlled with high precision, and thus the white balance of the captured image can be adjusted with the light source apparatus 5043. In addition, in this case, by irradiating the observation target with laser light from each of the RGB laser light sources in a time-division manner, and controlling the driving of the image sensor of the camera head 5005 in synchronization with the irradiation timing, it is also possible to capture images corresponding to R, G, and B in a time-division manner. According to such a method, color images can be obtained without providing the image sensor with a color filter.

In addition, the driving of the light source apparatus 5043 may also be controlled so as to change the intensity of the light to be output whenever a predetermined time elapses. By controlling the driving of the image sensor of the camera head 5005 in synchronization with the timing of changing the light intensity to acquire images in a time-division manner, and combining the images together, it is possible to generate a high dynamic range image without what are called crushed blacks and blown-out whites.

In addition, the light source apparatus 5043 may also be configured to be capable of supplying light in a predetermined wavelength band which is compatible with special light observation. With special light observation, for example, the wavelength dependency of light absorption by tissues of the body is utilized, and light is radiated in a narrow band compared to the irradiating light during normal observation (that is, white light) to thereby image predetermined tissues, such as blood vessels in the superficial portion of the mucous membrane, at a high contrast, also known as narrow band imaging (NBI). Alternatively, with special imaging, fluorescent observation that obtains an image with fluorescent light caused by radiating excitation light may also be conducted. With fluorescent observation, it is possible to irradiate a body tissue with excitation light and observe fluorescent light from the body tissue (auto-fluorescence observation), or locally inject a reagent such as indocyanine green (ICG) into a body tissue while also irradiating that body tissue with excitation light corresponding to the fluorescence wavelength of the reagent to obtain a fluorescent image, or the like. The light source apparatus 5043 can be configured to be capable of supplying narrow-band light and/or excitation light corresponding to such special imaging.

4. Feature of Trouble Determination According to Present Embodiment

Figure 12:
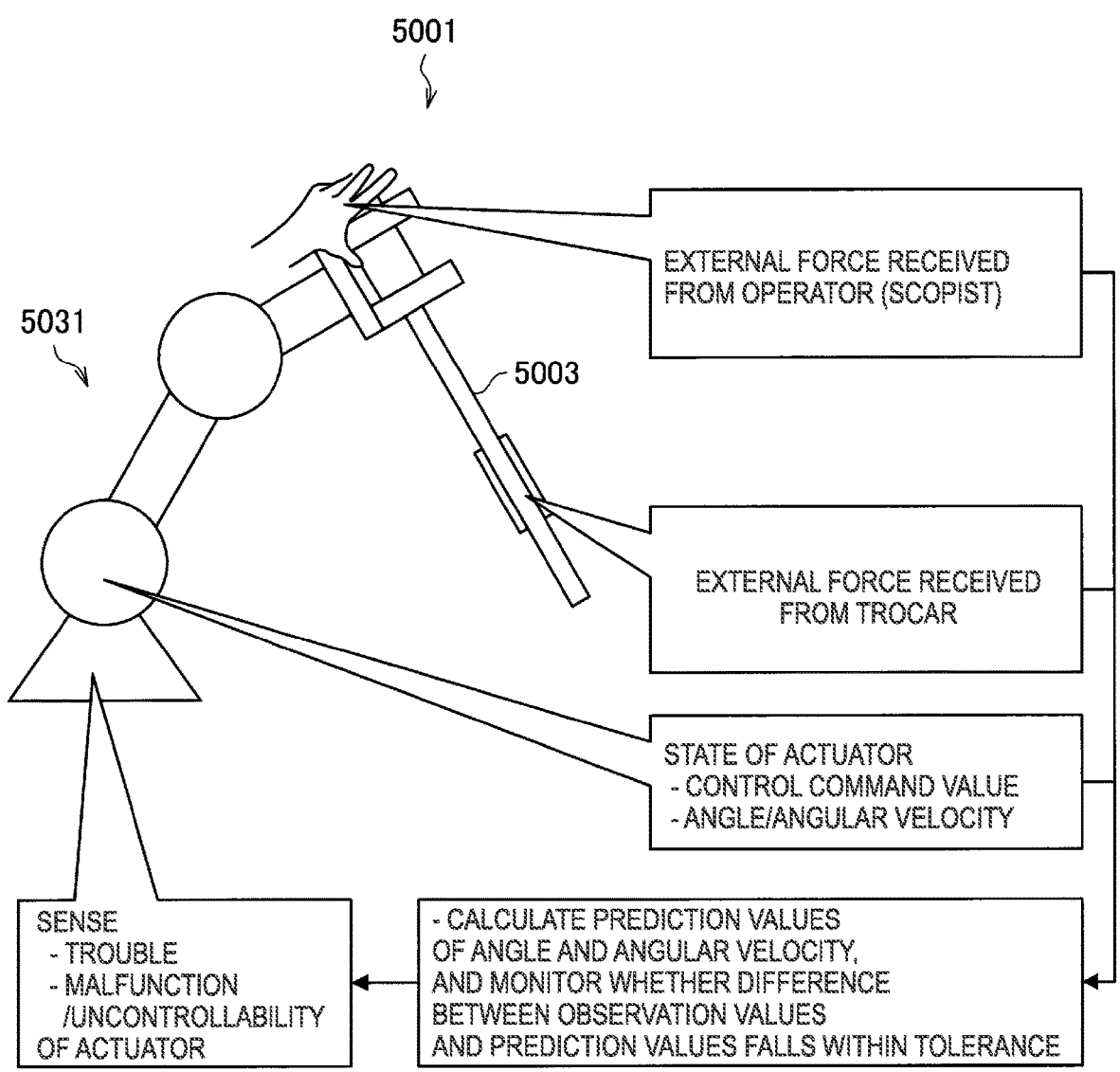
FIG. 12 is a schematic diagram for describing a feature of trouble determination according to the present embodiment.

FIG. 12 is a schematic diagram for describing a feature of trouble determination according to the present embodiment.

FIG. 12 illustrates the system illustrated in FIG. 13. The endoscope 5001 is mounted on the arm section 5031. As illustrated in FIG. 12, the endoscope 5001 receives external force caused by an operation performed by a surgeon (scopist). In addition, as illustrated in FIG. 13, the endoscope 5001 receives external force from the trocar 5025a by the lens barrel 5003 thereof being inserted into the trocar 5025a.

As shown in Equation (13), these kinds of external force are taken into consideration to calculate a prediction value as torque $\tau_e$. Thus, according to the present embodiment, it is possible to accurately predict an encoder value and a torque value even in the state in which external force is applied.

Laparoscopic surgery has been widely performed in recent years instead of laparotomy because laparoscopic surgery is minimally invasive. As illustrated in FIG. 13, laparoscopic surgery requires approximately one to three small holes (ports) to be made on the abdomen of a patient, and surgical instruments such as a rigid endoscope and forceps to be inserted into trocars installed at the ports for surgery. At this time, an operation on the endoscope 5001 to maintain the position/attitude of the endoscope 5001 or change the field of vision as required is performed by an expert doctor called a scopist. In such surgery, an endoscopic supporting arm apparatus is expected to assist a scopist in working or be used instead of it. The endoscopic supporting arm apparatus is required not only to support a doctor/scopist, but also be remarkably safe so as not to harm a patient. Therefore, it is desirable to definitely determine a break of a sensor installed in the supporting arm apparatus. However, the endoscopic arm receives external force from a plurality of places such as a drape wrapping the arm to separate the arm from the clean region, a scopist operating the arm, and further a trocar into which the arm is inserted, so that it is not possible to easily sense sensor trouble with the existing technology. In the present embodiment, it is possible to continuously predict/estimate a sensor value and detect sensor trouble even in such a situation.

Surgical microscopic operations are widely performed for neurosurgical and plastic-surgical treatment. To securely support a doctor, it is of crucial importance for the microscopic supporting arm as illustrated in FIG. 1 that sensor trouble is sensed. However, external force is applied from a plurality of places such as a drape wrapping the arm to separate the arm from the clean region and a doctor operating the arm, so that it is not possible to easily perform trouble detection with the existing technology. According to the present embodiment, it is possible to continuously predict/estimate a sensor value and detect sensor trouble even in such a situation.

Moreover, as a surgical robot, force received from an affected site or the like on which forceps or the like act also has to be taken into consideration in addition to external force generated by the components illustrated in FIGS. 1 and 13. In the present embodiment, it is possible to continuously predict a sensor value even if this point is taken into consideration.

5. Hardware Configuration

Figure 14:
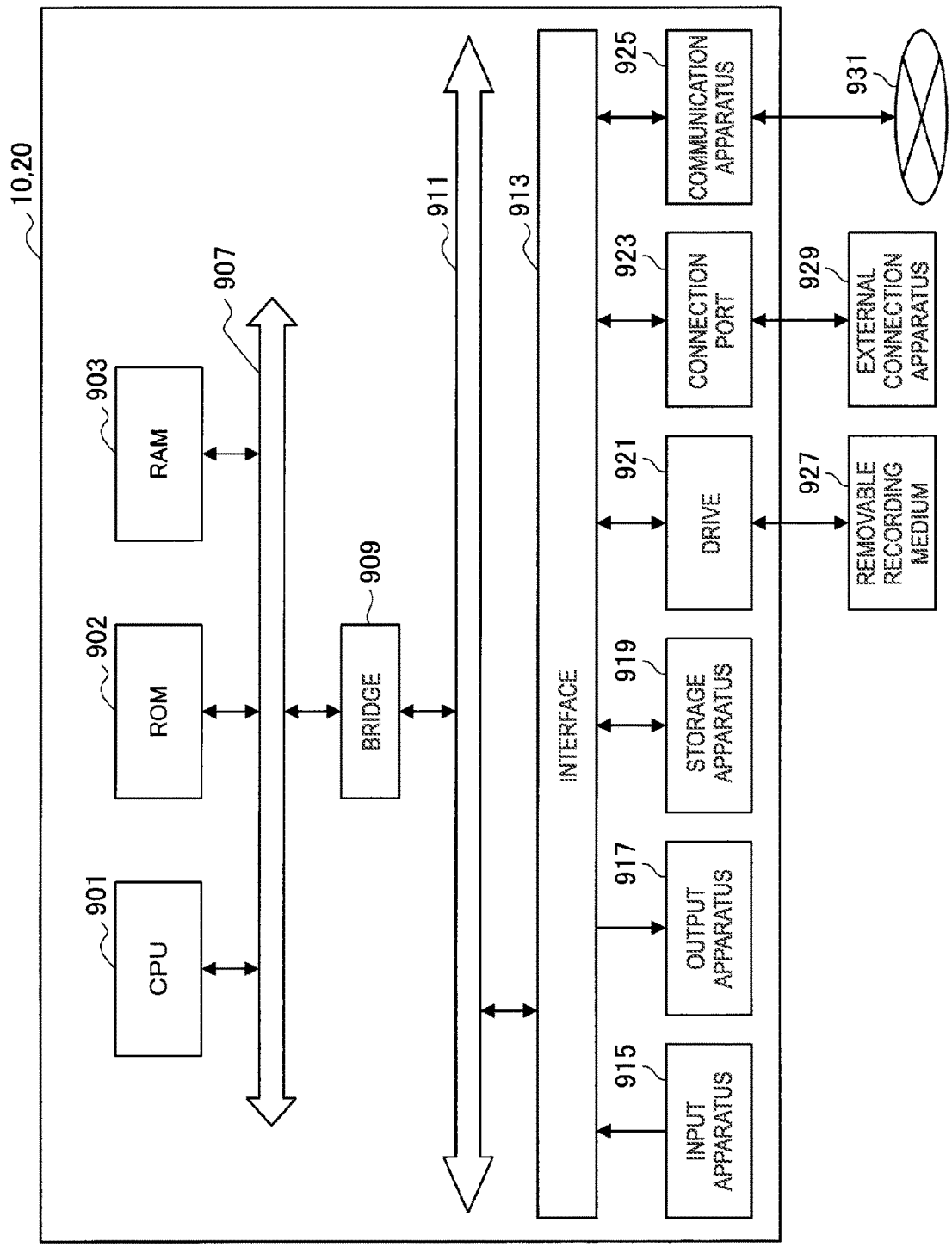
FIG. 14 is a functional block diagram illustrating an exemplary configuration of a hardware configuration of a supporting arm apparatus 10 and a control apparatus 20 according to an embodiment of the present disclosure.

Next, with reference to FIG. 14, the hardware configurations of the supporting arm apparatus 10 and control apparatus 20 according to the present embodiment illustrated in FIG. 6 will be described in detail. FIG. 14 is a functional block diagram illustrating a configuration example of the hardware configurations of the supporting arm apparatus 10 and control apparatus 20 according to an embodiment of the present disclosure.

The supporting arm apparatus 10 and the control apparatus 20 mainly include a CPU 901, a ROM 903, and a RAM 905. The supporting arm apparatus 10 and the control apparatus 20 further include a host bus 907, a bridge 909, an external bus 911, an interface 913, an input apparatus 915, an output apparatus 917, a storage apparatus 919, a drive 921, a connection port 923, and a communication apparatus 925.

The CPU 901 functions as an arithmetic processing apparatus and a control apparatus, and controls all or some operations of the supporting arm apparatus 10 and the control apparatus 20 according to various kinds of programs recorded in the ROM 903, the RAM 905, the storage apparatus 919, or a removable recording medium 927. The ROM 903 stores a program, an operation parameter, or the like used by the CPU 901. The RAM 905 primarily stores a program used by the CPU 901, a parameter that appropriately changes in execution of a program, or the like. The above-mentioned components are connected with one another by the host bus 907 including an internal bus such as a CPU bus. The CPU 901 corresponds to, for example, the arm control section 110 and the control section 230 illustrated in FIG. 6 in the present embodiment.

The host bus 907 is connected to the external bus 911 such as a peripheral component interconnect/interface (PCI) bus through the bridge 909. Further, the input apparatus 915, the output apparatus 917, the storage apparatus 919, the drive 921, the connection port 923, and the communication apparatus 925 are connected to the external bus 911 via the interface 913.

The input apparatus 915 is an operating means used by the user such as a mouse, a keyboard, a touch panel, a button, a switch, a lever, or a pedal. For example, the input apparatus 915 may be a remote control means (a so-called remote controller) using infrared light or any other radio waves, and may be an external connection device 929 such as a mobile telephone or a PDA corresponding to an operation of the supporting arm apparatus 10 and the control apparatus 20. Further, for example, the input apparatus 915 includes an input control circuit that generates an input signal on the basis of information input by the user using the operating means, and outputs the input signal to the CPU 901. The user of the supporting arm apparatus 10 and the control apparatus 20 can input various kinds of data to the supporting arm apparatus 10 and the control apparatus 20 or instruct the supporting arm apparatus 10 and the control apparatus 20 to perform a processing operation by operating the input apparatus 915. For example, the input apparatus 915 corresponds to the input section 210 illustrated in FIG. 6 in the present embodiment. Further, in the present embodiment, the purpose of motion in driving of the arm section 120 may be set by an operation input through the input apparatus 915 by the user, and the whole body cooperative control may be performed according to the purpose of motion.

The output apparatus 917 includes an apparatus capable of visually or acoustically notifying the user of the acquired information. As such an apparatus, there are a display apparatus such as a CRT display apparatus, a liquid crystal display apparatus, a plasma display apparatus, an EL display apparatus or a lamp, an audio output apparatus such as a speaker or a headphone, a printer apparatus, and the like. For example, the output apparatus 917 outputs a result obtained by various kinds of processes performed by the supporting arm apparatus 10 and the control apparatus 20. Specifically, the display apparatus displays a result obtained by various kinds of processes performed by the supporting arm apparatus 10 and the control apparatus 20 in the form of text or an image. Meanwhile, the audio output apparatus converts an audio signal including reproduced audio data, acoustic data, or the like into an analogue signal, and outputs the analogue signal. In the present embodiment, various kinds of information related to driving control of the arm section 120 may be output from the output apparatus 917 in all forms. For example, in driving control of the arm section 120, the trajectory of movement of each component of the arm section 120 may be displayed on the display screen of the output apparatus 917 in the form of a graph. Note that the display apparatus 30 illustrated in FIG. 6, for example, may be an apparatus including the function and configuration of the output apparatus 917 serving as the display apparatus and a component such as a control section for controlling driving of the display apparatus.

The storage apparatus 919 is a data storage apparatus configured as an exemplary storage section of the supporting arm apparatus 10 and the control apparatus 20. For example, the storage apparatus 919 includes a magnetic storage section device such as a hard disk drive (HDD), a semiconductor storage device, an optical storage device, a magneto optical storage device, or the like. The storage apparatus 919 stores a program executed by the CPU 901, various kinds of data, and the like. For example, the storage apparatus 919 corresponds to the storage section 220 illustrated in FIG. 6 in the present embodiment. Further, in the present embodiment, the storage apparatus 919 may store the operation condition (the purpose of motion and the constraint condition) in the operation related to the whole body cooperative control using the generalized inverse dynamics, and the supporting arm apparatus 10 and the control apparatus 20 may perform the operation related to the whole body cooperative control using the operation condition stored in the storage apparatus 919.

The drive 921 is a recording medium reader/writer, and is equipped in or attached to the supporting arm apparatus 10 and the control apparatus 20. The drive 921 reads information stored in the removable recording medium 927 mounted thereon such as a magnetic disk, an optical disc, a magneto optical disc, or a semiconductor memory, and outputs the read information to the RAM 905. Further, the drive 921 can write a record in the removable recording medium 927 mounted thereon such as a magnetic disk, an optical disk, a magneto optical disk, or a semiconductor memory. For example, the removable recording medium 927 is a DVD medium, an HD-DVD medium, a Blu-ray (a registered trademark) medium, or the like. Further, the removable recording medium 927 may be a Compact Flash (CF) (a registered trademark), a flash memory, a Secure Digital (SD) memory card, or the like. Furthermore, for example, the removable recording medium 927 may be an integrated circuit (IC) card equipped with a non-contact type IC chip, an electronic device, or the like. In the present embodiment, various kinds of information related to driving control of the arm section 120 is read from various kinds of removable recording media 927 or written in various kinds of removable recording media 927 through the drive 921.

The connection port 923 is a port for connecting a device directly with the supporting arm apparatus 10 and the control apparatus 20. As an example of the connection port 923, there are a Universal Serial Bus (USB) port, an IEEE1394 port, a Small Computer System Interface (SCSI) port, and the like. As another example of the connection port 923, there are an RS-232C port, an optical audio terminal, a High-Definition Multimedia Interface (HDMI) (a registered trademark), and the like. As the external connection device 929 is connected to the connection port 923, the supporting arm apparatus 10 and the control apparatus 20 acquire various kinds of data directly from the external connection device 929 or provide various kinds of data to the external connection device 929. In the present embodiment, various kinds of information related to driving control of the arm section 120 may be read from various kinds of external connection devices 929 or written in various kinds of external connection devices 929 through the connection port 923.

For example, the communication apparatus 925 is a communication interface including a communication device or the like used for a connection with a communication network (network) 931. For example, the communication apparatus 925 is a communication card for a wired or wireless local area network (LAN), Bluetooth (a registered trademark), or wireless USB (WUSB). Further, the communication apparatus 925 may be an optical communication router, an asymmetric digital subscriber line (ADSL) router, various kinds of communication modems, or the like. For example, the communication apparatus 925 can transmit or receive a signal to or from the Internet or another communication apparatus, for example, according to a certain protocol such as TCP/IP. Further, the communication network 931 connected to the communication apparatus 925 includes a network connected in a wired or wireless manner, and may be, for example, the Internet, a domestic LAN, infrared ray communication, radio wave communication, satellite communication, or the like. In the present embodiment, various kinds of information related to driving control of the arm section 120 may be transmitted or received to or from another external device via the communication network 931 through the communication apparatus 925.

The hardware configuration capable of implementing the functions of the supporting arm apparatus 10 and the control apparatus 20 according to an embodiment of the present disclosure has been described above. Each of the above components may be configured using a versatile member, and may be configured by hardware specialized for the function of each component. Thus, the hardware configuration to be used may be appropriately changed according to a technology level when the present embodiment is carried out. Note that, although not illustrated in FIG. 14, the supporting arm apparatus 10 obviously includes various kinds of components corresponding to the arm section 120 illustrated in FIG. 6.

Note that it is possible to create a computer program for implementing the functions of the supporting arm apparatus 10 according to the present embodiment, the control apparatus 20, and the display apparatus 30 and install the computer program in a personal computer or the like. Furthermore, it is possible to provide a computer readable recording medium storing the computer program as well. Examples of the recording medium include a magnetic disk, an optical disc, a magneto optical disc, and a flash memory. Further, for example, the computer program may be delivered via a network without using the recording medium.

6. Conclusion

The microscopic supporting arm as illustrated in FIG. 1 which has a microscope installed at the front edge has abundant opportunity to receive force from the outside of the arm during operations like external force received from a drape, external force received at the time of an arm operation for changing the observation field, or the like. According to the present embodiment, it is possible to continuously predict a sensor value even in the case where such external force is received.

The endoscope holder supporting arm as illustrated in FIG. 13 which has an endoscope holder installed at the front edge has abundant opportunity to receive force from the outside of the arm during operations like external force received from a trocar with which the endoscope comes into contact, or the like in addition to the case of the microscopic supporting arm. According to the present embodiment, it is possible to continuously predict a sensor value even in such a case.

Moreover, a surgical supporting arm and a supporting arm that have forceps/catheters or the like installed at the front edges has abundant opportunity to receive force from the outside of the arm like external force received from an affected side with which a surgical instrument comes into contact or the like in addition to the examples of a microscopic supporting arm and an endoscope holder supporting arm. According to the present embodiment, it is possible to continuously predict a sensor value even in such a case.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A control apparatus including:

a prediction section configured to, in an actuator including a torque sensor that detects torque generated at a driving shaft, and an encoder that detects a rotational angle of the driving shaft, predict a detection value of the encoder on a basis of a detection value of the torque sensor, or predict the detection value of the torque sensor on a basis of the detection value of the encoder; and a trouble determination section configured to compare a prediction value predicted by the prediction section with an actually measured value of the torque sensor or the encoder to perform trouble determination on the torque sensor or the encoder.

(2)

The control apparatus according to (1), in which the prediction section includes an encoder prediction value calculation section that predicts the detection value of the encoder on the basis of the detection value of the torque sensor.

(3)

The control apparatus according to (1) or (2), in which the prediction section includes a torque sensor prediction value calculation section that predicts the detection value of the torque sensor on the basis of the detection value of the encoder.

(4)

The control apparatus according to (1), in which the prediction section uses generated torque and external force generated by the actuator at the driving shaft to predict the detection value of the encoder or the detection value of the torque sensor on a basis of an equation of motion that defines a relationship between the external force and the torque generated at the driving shaft, angular velocity of the actuator, and angular acceleration of the actuator.

(5)

The control apparatus according to (2), in which the encoder prediction value calculation section uses generated torque and external force generated by the actuator at the driving shaft to predict the detection value of the encoder on a basis of an equation of motion that defines a relationship between external force torque generated at the driving shaft, angular velocity of the actuator, and angular acceleration of the actuator.

(6)

The control apparatus according to (5), in which the encoder prediction value calculation section predicts the detection value of the encoder for each predetermined control cycle, and predicts, on a basis of the equation of motion, the angular acceleration in a next cycle on a basis of the generated torque in a current cycle, the external force torque in the current cycle, and the angular velocity in the current cycle.

(7)

The control apparatus according to (3), in which the torque sensor prediction value calculation section uses generated torque and external force generated by the actuator at the driving shaft to predict the detection value of the torque sensor on a basis of an equation of motion that defines a relationship between external force torque generated at the driving shaft, angular velocity of the actuator, and angular acceleration of the actuator.

(8)

The control apparatus according to (7), in which the torque sensor prediction value calculation section predicts the detection value of the torque sensor for each predetermined control cycle, and predicts, on a basis of the equation of motion, the external force torque in a previous cycle on a basis of the generated torque in the previous cycle, the angular velocity in the previous cycle, and the angular acceleration in a current cycle.

(9)

The control apparatus according to any of (1) to (8), in which the trouble determination section performs the trouble determination in a case where a difference between a value predicted by the prediction section and an actually measured value of the torque sensor or the encoder is greater than or equal to a predetermined threshold.

(10)

The control apparatus according to any of (1) to (9), in which the actuator drives a joint section of a supporting arm on which a medical instrument is mounted.

(11)

A control method including:
predicting, in an actuator including a torque sensor that detects torque generated at a driving shaft, and an encoder that detects a rotational angle of the driving shaft, a detection value of the encoder on a basis of a detection value of the torque sensor, or predicting the detection value of the torque sensor on a basis of the detection value of the encoder; and
comparing the predicted value with an actually measured value of the torque sensor or the encoder to perform trouble determination on the torque sensor or the encoder.

REFERENCE SIGNS LIST 262 encoder prediction value calculation section
264 torque sensor prediction value calculation section
266 sensor trouble determination section

The invention claimed is:

1. A control apparatus, comprising:
a prediction section in an actuator, wherein
the actuator includes a torque sensor that detects torque generated at a driving shaft, and an encoder that detects a rotational angle of the driving shaft, and
the prediction section is configured to:
predict a first detection value of the encoder in a next cycle based on a first detection value of the torque sensor and a torque command value in a current cycle, wherein
the torque command value is based on the detected rotational angle of the driving shaft and the torque generated at the driving shaft, and
the next cycle is subsequent to the current cycle; and
predict a second detection value of the torque sensor based on a second detection value of the encoder; and
a trouble determination section configured to:
compare the predicted first detection value of the encoder with a measured value of the encoder to perform trouble determination on the encoder; and
compare the predicted second detection value of the torque sensor with a measured value of the torque sensor to perform trouble determination on the torque sensor.

2. The control apparatus according to claim 1, wherein the prediction section includes an encoder prediction value calculation section configured to predict the first detection value of the encoder in the next cycle based on the first detection value of the torque sensor and the torque command value in the current cycle.

3. The control apparatus according to claim 2, wherein the encoder prediction value calculation section is further configured to predict the first detection value of the encoder in the next cycle based on an equation of motion that defines a relationship between external force generated by the actuator at the driving shaft, the torque command value in the current cycle, angular velocity of the actuator, and angular acceleration of the actuator.

4. The control apparatus according to claim 3, wherein the encoder prediction value calculation section is further configured to:
predict the angular acceleration of the actuator in the next cycle based on the equation of motion, the torque command value in the current cycle, external force torque in the current cycle, and the angular velocity of the actuator in the current cycle; and
predict the first detection value of the encoder for each control cycle based on the equation of motion.

5. The control apparatus according to claim 1, wherein the prediction section includes a torque sensor prediction value calculation section configured to predict the second detection value of the torque sensor based on the second detection value of the encoder.

6. The control apparatus according to claim 5, wherein
the torque sensor prediction value calculation section is further configured to predict the second detection value of the torque sensor based on an equation of motion that defines a relationship between external force torque at the driving shaft, the torque command value, angular velocity of the actuator, and angular acceleration of the actuator.

7. The control apparatus according to claim 6, wherein the torque sensor prediction value calculation section is further configured to:
predict the external force torque in a previous cycle based on the equation of motion, the torque command value in the previous cycle, the angular velocity of the actuator in the previous cycle, and the angular acceleration of the actuator in the current cycle, wherein
the current cycle is subsequent to the previous cycle; and
predict the second detection value of the torque sensor for each control cycle based on the equation of motion.

8. The control apparatus according to claim 1, wherein
the prediction section is further configured to predict the first detection value of the encoder and the second detection value of the torque sensor based on an equation of motion, and
the equation of motion defines a relationship between external force generated by the actuator at the driving shaft, the torque command value, angular velocity of the actuator, and angular acceleration of the actuator.

9. The control apparatus according to claim 1, wherein the trouble determination section is further configured to:
perform the trouble determination for the torque sensor based on a first difference between the predicted second detection value of the torque sensor and the measured value of the torque sensor, wherein the first difference is one of greater than or equal to a first threshold value; and
perform the trouble determination for the encoder based on a second difference between the predicted first detection value of the encoder and the measured value of the encoder, wherein the second difference is one of greater than or equal to a second threshold value.

10. The control apparatus according to claim 1, wherein the actuator drives a joint section of a supporting arm on which a medical instrument is mounted.

11. A control method, comprising:
predicting, in an actuator including a torque sensor that detects torque generated at a driving shaft, and an encoder that detects a rotational angle of the driving shaft, a first detection value of the encoder in a next cycle based on a first detection value of the torque sensor and a torque command value in a current cycle, wherein
the torque command value is based on the detected rotational angle of the driving shaft and the torque generated at the driving shaft, and
the next cycle is subsequent to the current cycle;
predicting a second detection value of the torque sensor based on a second detection value of the encoder;
comparing the predicted first detection value of the encoder with a measured value of the encoder to perform trouble determination on the encoder; and
comparing the predicted second detection value of the torque sensor with a measured value of the torque sensor to perform trouble determination on the torque sensor.

12. A control apparatus, comprising:
a prediction section, in an actuator including a torque sensor that detects torque generated at a driving shaft, and an encoder that detects a rotational angle of the driving shaft, configured to:
predict a detection value of the encoder based on a detection value of the torque sensor and a torque command value, or predict a detection value of the torque sensor based on the detection value of the encoder;
predict angular acceleration of the actuator in a next cycle based on an equation of motion, the torque command value in a current cycle, external force torque in the current cycle, and angular velocity of the actuator in the current cycle, wherein
the torque command value is based on the detected rotational angle of the driving shaft and the torque generated at the driving shaft,
the equation of motion defines a relationship between external force generated by the actuator at the driving shaft, the angular velocity of the actuator, and the angular acceleration of the actuator, and
the next cycle is subsequent to the current cycle; and
predict the detection value of the encoder for each control cycle based on the equation of motion, the torque command value, the angular velocity of the actuator, and the angular acceleration of the actuator; and
a trouble determination section configured to:
compare the predicted detection value of the encoder with a measured value of the encoder to perform trouble determination on the encoder, or
compare the predicted detection value of the torque sensor with a measured value of the torque sensor to perform trouble determination on the torque sensor.

13. A control apparatus, comprising:
a prediction section, in an actuator including a torque sensor that detects torque generated at a driving shaft, and an encoder that detects a rotational angle of the driving shaft, configured to:
predict a detection value of the encoder based on a detection value of the torque sensor and a torque command value, or predict a detection value of the torque sensor based on the detection value of the encoder;
predict external force torque of the actuator in a previous cycle based on an equation of motion, the torque command value in the previous cycle, angular velocity of the actuator in the previous cycle, and angular acceleration of the actuator in a current cycle, wherein
the torque command value is based on the detected rotational angle of the driving shaft and the torque generated at the driving shaft,
the equation of motion defines a relationship between the external force torque at the driving shaft, the angular velocity of the actuator, and the angular acceleration of the actuator, and
the current cycle is subsequent to the previous cycle; and
predict the detection value of the torque sensor for each control cycle based on the equation of motion, the torque command value, the angular velocity of the actuator, and the angular acceleration of the actuator; and a trouble determination section configured to:
  compare the predicted detection value of the encoder with a measured value of the encoder to perform trouble determination on the encoder, or
  compare the predicted detection value of the torque sensor with a measured value of the torque sensor to perform trouble determination on the torque sensor.

* * * * *